(12) United States Patent
Paolitto et al.

(10) Patent No.: US 6,517,563 B1
(45) Date of Patent: Feb. 11, 2003

(54) PERICARDIUM RETRACTION DEVICE FOR POSITIONING A BEATING HEART

(75) Inventors: Anthony Paolitto, St. Leonard (CA); Valerio Valentini, Montreal (CA); Raymond Cartier, Mount Royal (CA)

(73) Assignee: Coroneo, Inc., Montreal (CA)

( * ) Notice: Subject to any disclaimer, the term of this patent is extended or adjusted under 35 U.S.C. 154(b) by 0 days.

(21) Appl. No.: 09/763,026

(22) PCT Filed: Aug. 17, 1999

(86) PCT No.: PCT/CA99/00757
§ 371 (c)(1),
(2), (4) Date: Apr. 9, 2001

(87) PCT Pub. No.: WO00/10466
PCT Pub. Date: Mar. 2, 2000

(30) Foreign Application Priority Data

Aug. 17, 1998 (CA) .............................................. 2242766

(51) Int. Cl.[7] .............................................. A61B 17/00
(52) U.S. Cl. ...................................... 606/205; 600/206
(58) Field of Search ........................ 600/205, 37, 201, 600/204, 210, 219, 235, 207, 208; 606/193, 123, 166, 213; 128/897, 898

(56) References Cited

U.S. PATENT DOCUMENTS

| 5,727,569 A | 3/1998 | Benetti et al. |
| 5,782,746 A | 7/1998 | Wright |
| 6,019,722 A | * 2/2000 | Spence et al. |
| 6,032,672 A | * 3/2000 | Taylor |
| 6,090,041 A | * 7/2000 | Clark et al. |
| 6,336,898 B1 | * 1/2002 | Borst et al. |
| 6,338,710 B1 | * 1/2002 | Takahashi et al. |
| 6,338,712 B2 | * 1/2002 | Spence et al. |

FOREIGN PATENT DOCUMENTS

| WO | WO 96/40354 A | 12/1996 |
| WO | WO 98/40018 A | 9/1998 |

* cited by examiner

Primary Examiner—Pedro Philogene

(57) ABSTRACT

A surgical apparatus for suction attachment to a body tissue. The apparatus includes a tissue-engaging component defining a concave vacuum compartment. The vacuum compartment is connectable to a vacuum source. A valve selectively allows and prevents the generation of a vacuum in the vacuum compartment. The peripheral edge of the vacuum compartment is attachable by suction to the body tissue when the vacuum is generated. A valve closing arrangement automatically closes the valve upon the peripheral edge being separated from the body tissue so as to maintain vacuum generating efficiency for the other tissue-engaging components coupled to the same vacuum source.

30 Claims, 15 Drawing Sheets

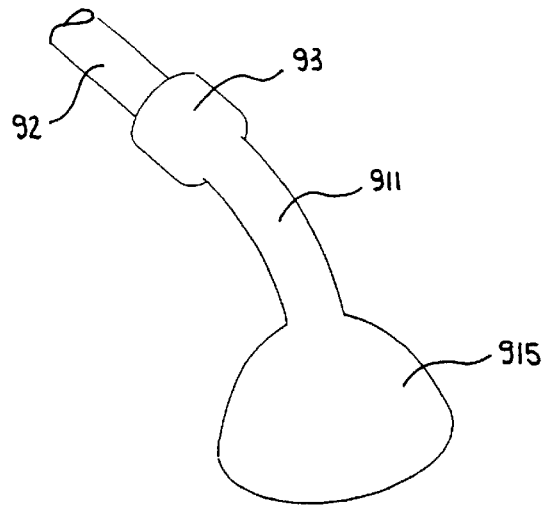
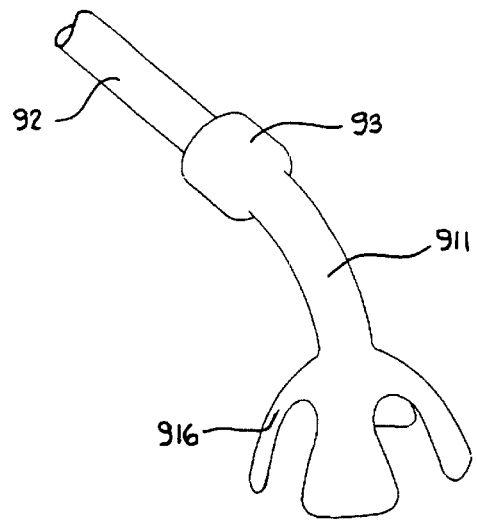
*Figure 12A*
*Figure 12B*
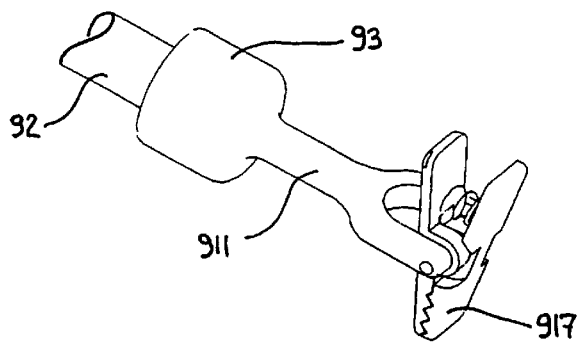
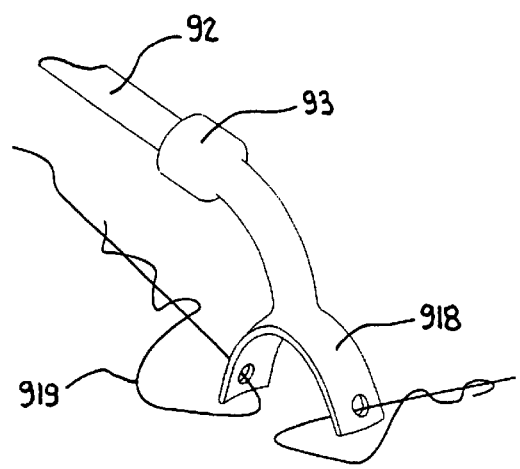
*Figure 12C*
*Figure 12D*

PERICARDIUM RETRACTION DEVICE FOR POSITIONING A BEATING HEART

FIELD OF THE INVENTION

The present invention relates to the field of surgical apparatus and more specifically, to a tissue retraction device for positioning and orienting a beating heart during cardiac surgery.

BACKGROUND OF THE INVENTION

Coronary artery bypass graft (CABG) surgery is a widely practised surgical procedure for performing coronary artery revascularization or bypass grafts. This surgical procedure consists of replenishing or augmenting blood flow to a portion of the patient's heart which is being deprived of such flow due to a restriction or blockage in a coronary artery supplying the said portion of the patient's heart. A healthy segment from a blood vessel, such as an artery or a vein converted into an artery, is attached to the patient's vasculature from a point upstream of the coronary artery restriction or blockage to a point downstream thereof, thereby creating the bypass artery and associated bypass blood flow. Since the great majority of CABG surgeries are multi-vessel bypasses, this surgical procedure remains one of the most common and effective treatments for coronary artery disease.

Traditional CABG surgery has been commonly performed through a midline sternotomy incision, where the patient's sternum is incised and the ribcage retracted to obtain access mainly to the patient's heart, the coronary vessels, and other internal thoracic arteries. Intercostal thoracotomy approaches have also been employed whereby two adjacent ribs are spread apart, at times even removing a length of rib to improve access into the patient's thorax. In both approaches, a surgical retractor is used to spread the patient's skin and bone structure and to maintain an incised opening or surgical window onto the underlying heart and coronary vessels.

CABG surgery has been traditionally performed with the support of a cardio-pulmonary machine, whereby the patient's blood is oxygenated outside the body through extracorporeal circulation (ECC). This allows the surgeon to perform surgical procedures on a near perfectly still heart while the patient's life support is maintained by cardiopulmonary assistance. During traditional CABG surgery, the surgeon or assistant may manually or otherwise manipulate the arrested heart into a position and orientation that yields the best access to the target artery requiring the bypass graft. The great majority of CABG surgeries (approximately 70%) are triple vessel bypass surgeries; that is, at least one bypass graft is performed on each of the anterior, inferior and posterior artery beds of the patient's heart.

Recently, in an aim to render CABG surgery less invasive to the patient, beating heart CABG surgery is being developed whereby ECC, one of the most invasive aspects of cardiac surgery, is eliminated and coronary artery revascularization is performed directly on the beating heart. One of the challenges in performing beating heart CABG surgery lies in positioning and orienting the beating heart in order to obtain access to the inferior and posterior artery beds, while aiming to minimize physiologically undesirable effects such as hemodynamic instability, arrhythmia, or a precipitous drop in arterial pressure, any of which may occur as a result of such beating heart manipulation. Furthermore, a surgical device which enables manipulation of the beating heart or which restrains its movement or positioning may impose loads and constraints on the beating heart. This may impede the normal beating function of the heart and induce the onset of the physiologically undesirable effects described above. In traditional CABG surgery, the heart is arrested and therefore heart manipulations are well tolerated.

During CABG surgery or beating heart CABG surgery, the pericardium, namely the substantially thin membranous tissue forming a sac in which the heart and the commencement of the major blood vessels connecting with the heart are contained, is generally incised and unraveled to expose at least a portion of the heart surface which is to receive the bypass graft. The pericardium tissue, unlike the heart, is not beating and it may be separated from the heart surface except in certain locations where it is anatomically attached to the heart. Thus, it is surgically possible in CABG surgery to position and orient the heart through retraction, positioning and loading of the pericardium tissue to obtain access to the inferior and posterior coronary artery beds. In beating heart CABG, heart manipulations achieved through retraction of the pericardium tissue tends to reduce the likelihood of inducing trauma to the beating heart and tends to minimize the physiologically undesirable effects mentioned above, since direct contact with the beating heart is avoided. One such beating heart manipulation consists of "verticalizing" the heart in order to gain access to the posterior artery bed. In this maneuver, the pericardium is engaged close to the base of the heart, preferably 1.5 inches from pericardial reflection, and the apex of the heart is rotated outward from retracted chest cavity through the tensile loads applied to the engaged pericardium. The longitudinal axis of the beating heart thereby assumes a substantially vertical orientation.

The desired position and orientation of a beating heart may be maintained, at least in part, by maintaining retraction loads applied to the pericardium tissue and securing the surgical apparatus that applies the tensile load to pericardium tissue. During CABG surgery, a deployed surgical retractor provides a suitable stable platform for the securement of the pericardium retraction loads. The pericardium tissue may be engaged by a variety of methods. Sutures such as traction or stay sutures have been generally employed in cardiac surgery to retract tissue during a surgical intervention. Traditionally sutures consist of tissue piercing member such as a relatively sharp needle and a length of wire-like filament such as a suture line integrally attached to the blunt end of said needle. Pericardium retraction may be achieved through the application of pericardial traction sutures whereby the needle pierces the pericardium tissue, threading a certain length of suture line through the pierced pericardium tissue, and pulling simultaneously on both the resulting lengths of suture line; that is, the length between the pierced tissue and the free end of the suture line, and the length between the pierced tissue and the needle-bearing end of the suture line, to displace the pericardium tissue and consequently the beating heart anatomically attached to the pericardium.

In order to "verticalize" a beating with pericardial traction sutures, a number of such sutures must be inserted through and engaged with the pericardium tissue preferably along its pericardial reflection in order to get the desired lifting of the heart apex and consequently the best exposure to the posterior coronary bed. For example, one traction suture may be placed between the superior and inferior pulmonary vein, a second one below the inferior pulmonary vein, a third one midway between the apex of the heart and the inferior pulmonary vein, and a fourth one towards the diaphragmatic face near the inferior vena cava. Pericardium retraction loads are subsequently applied to each of these traction sutures independently. The resulting lengths of suture line must then be secured to a stable surgical platform such as the sternum retractor to maintain the desired retraction load on the pericardium tissue.

During the placement of these pericardial traction sutures deep within the patient's thorax and close to the base of the beating heart, the surgeon's view of the body tissue contained beyond the unraveled pericardium tissue is hindered. Consequently, because of this blind installation, the risk of unintentionally puncturing other underlying body tissue with the tissue piercing needle may lead to operative or postoperative complications, especially when a number of such sutures is required. For instance, an inadvertent puncture of the pleura and lungs may lead to a pneumothorax injury if undetected. The placement of deep pericardial traction sutures may therefore be challenging.

Pericardial traction sutures may be characterized by additional drawbacks. For example the placement of such sutures may be time consuming, since securing of the pericardium retraction load through the manual tying of the suture line lengths is often a multiple step threading and knotting procedure. As well, the placement of pericardial traction sutures may in some instances be cumbersome due to poor access to the deeper portions of pericardial tissue and due to the number of traction sutures required to achieve beating heart "verticalization". Lastly, these sutures may not be conducive to permitting easy readjustment of the magnitude of the desired tensile load on the pericardium tissue, or of the direction of said load relative to the pericardium tissue. Typically readjustments of this type may require a surgeon to untie and retie suture line lengths or to cut the existing suture line having the undesired retraction load and replace it with a new suture that must repierce the pericardium tissue and again be secured.

Generally, adjustment of the desired tensile load on the pericardium tissue by cutting an existing suture line and repiercing a new suture line is not desirable. First, the process of placing a pericardial traction suture requires considerable manual dexterity, at times requiring the help of an assistant. The process is therefore tedious and time consuming. Second, a repiercing of the pericardium tissue with a subsequent traction suture tends to increase the likelihood of inducing tissue trauma or tissue tearing which may have to be surgically repaired.

Based on the foregoing, it would be advantageous to provide a means for pericardium retraction which is less invasive to the pericardium tissue and underlying coronary tissue, and which is not compromised by a surgeon's lack of vision behind the pericardium tissue. Since the pericardium is a relatively thin, membranous tissue which is incised and unraveled to expose the underlying heart surface prior to performing cardiac surgery, it would be advantageous to have the pericardium tissue engaged by a negative pressure suction force. It would be a further advantage to have the pericardium contacting perimeter of the negative pressure suction device constructed from a substantially flexible material which conforms to variations in anatomy, and which deflects to form a substantial seal when placed in contact with the pericardium and activated by a negative pressure suction force.

Subsequent to securing the desired position and orientation of the beating heart through retraction of the pericardium tissue, coronary artery revascularization may be achieved by locally immobilizing a small portion of the beating heart around the target artery requiring the bypass graft through a variety of ways. One such method consists of immobilizing the portion of beating heart around the target artery through the application of a mechanical compression by virtue of a coronary stabilizer. The remaining portions of the heart continue to beat while the target artery site is immobilized during the bypass graft procedure. One such surgical apparatus for achieving this method of mechanical immobilization has been described in copending Canadian patent application Serial No. 2,216,893 filed on Sep. 30, 1997 in the names of Cartier and Paolitto and entitled "Sternum Retractor for Performing Bypass Surgery on a Beating Heart". Alternatively, a negative pressure suction has also been used in beating heart CABG to locally immobilize a portion of the beating heart surface in the vicinity of the target artery requiring the bypass graft. An associated device which applies the suction force to the beating heart surface is subsequently secured relative to a stable platform. In this case, the suction port or the structural members of the associated device that applies the negative pressure force must be substantially rigid since the primary purpose of the device is to attempt to immobilize and render motionless that portion of heart tissue it engages in order to create a stable surgical field, while the rest of the heart continues to beat.

U.S. Pat. No. 5,727,569 issued to Benetti et al. on Mar. 17, 1998 and entitled "Surgical Devices for Imposing a Negative Pressure to Fix the Position of Cardiac Tissue during Surgery", describes a surgical device for imposing a negative pressure directly on a portion of the outer surface of the beating heart. The Benetti device is applied proximate to or surrounding the portion of the outer surface of the beating heart at which a surgical intervention is to occur. By applying negative pressure by means of the Benetti device, the motion of the outer surface of the beating heart is restricted at the particular area where the surgeon is working. The Benetti reference therefore relates to alleviating the problem of performing extremely delicate surgical procedures, like bypass grafting, during which contractions of the beating heart cause the target artery surface of the heart to move continuously. Benetti et al. teach a method of locally and directly immobilizing the target artery location during a surgical intervention intended to occur within the immobilized region.

In contrast to the teachings of the prior art, the present invention herein described relates to surgical manipulation of the pericardium, which is the substantially conical membranous sac in which the heart and the commencement of the major vessels are contained. The Benetti reference does not teach or suggest the positioning and orienting of the entire beating heart as a whole, nor is there any teaching or suggestion therein of retraction of the pericardium to achieve surgical access in an area of the beating heart away from where pericardium retraction device is deployed. Rather, Benetti et al. apply suction around or close to the portion of beating heart tissue proximal to the area where the surgical intervention is to be performed. More specifically, the teachings of Benetti et al. result in immobilization of the pulsating effects of a portion of the exterior surface of the beating heart through negative force application at the target artery site. It would be advantageous to be able to position the beating heart through the deployment of the device in a location remote to the desired site of surgical intervention to tend to facilitate the access and approach of surgical instruments, and to tend to improve the ergonomics of the grafting site and direct visibility thereto. Unlike the teachings of the Benetti reference, which results in the application of suction directly on the beating heart, it would instead be advantageous to apply this suction indirectly on a benign, non-beating part of coronary organ tissue. This will tend to not impede, restrain or restrict the function of the beating heart.

Benetti et al. describe a device with multiple suction ports attached through a negative pressure manifold. In the teachings of Benetti, it is suggested to provide a device having suction ports which share a common negative pressure manifold. However, in such a suggested device, if one suction port is not in contact with underlying tissue to form a seal, then the entire system will tend to be rendered ineffective, at least in part, by the leakage through said port. It would be advantageous to introduce a feature which cuts off flow through non-sealing suction ports with cardiac tissue, thereby tending to maintain effective the entire set-up even if only a portion of the suction ports are properly sealing with the said tissue. Alternatively, Benetti et al. teach that each suction port can have it own independent supply line, which would circumvent this problem through a more complex, cumbersome, and part-intensive set-up. The new invention described herein introduces an embodiment thereof which allows the surgical apparatus, namely the pericardium retraction device, to function with at least a portion of the suction ports in contact with the coronary organ tissue. This embodiment can be applied to other surgical apparatus engaging coronary organ tissue through a negative pressure suction force.

The Benetti reference describes either fixing the suction port device to a rigid support during the procedure, or having the suction port device as a part of a hand-held instrument with a handle structure connected thereto and adapted to being grasped by a human hand. In contrast to the teachings and suggestions of the Benetti reference, it may be advantageous to attach a suction port device to an intermediate positioning means prior to fixturing the complement to a stable surgical platform such as a sternum retractor, in order to achieve flexibility in the surgical set-up to attempt to cater said surgical set-up to distinct patient anatomies.

According to the Benetti teachings, the negative pressure suction is the only input means for activating the device to engage the underlying beating heart tissue. If the suction is lost, the loss will lead to the surgical work-site of the beating heart no longer immobilized and resulting instability from pulsating effects. If other instruments are in contact with the heart at this time, it may also lead to risk of trauma or injury.

In the pericardium retraction device according to the present invention, it would be advantageous to have a design feature in the tissue-engaging member that is activated by the negative pressure suction therein, whereby said design feature comes into contact with a portion of the engaged pericardium tissue and is capable of transmitting a mechanical force to the pericardium tissue being retracted. It would be a further advantage if this said mechanical force remains as a back-up feature in the eventuality that the suction force is interrupted or lost. The embodiment of the invention described herein can be applied to all other surgical apparatus engaging coronary organ tissue.

In "verticalizing" the beating heart through retraction of pericardium tissue, it may be advantageous in some instances to incorporate in the pericardium retraction device a bracing member which engages on the apex of the "verticalized" beating heart, and thereby tends to facilitate in-process re-adjustments of the position and orientation of the entire beating heart by the movement of the surgical apparatus comprising the pericardium retraction device together with the apex-bracing member.

In light of the foregoing it would therefore be advantageous to have a device which acts on a portion of the pericardium tissue, in a location remote to the target artery site where the surgical intervention will take place, to aim to achieve the beating heart manipulations in a least invasive, hemodynamically stable manner, wherein the device would not materially interfere with the normal beating function of the heart. It would be a further advantage if this device would act in an area remote to where the surgical intervention is to occur, thereby tending to improve the surgeon's direct vision and ergonomics of the surgical work-site.

Although the present invention will focus on cardiac surgery, and more specifically CABG surgery performed directly on a beating heart, the principles and concepts may be applied to other types of surgery or surgical interventions that may benefit from the positioning and orientation of a body organ through the retraction of membrane-like body tissue anatomically attached to the said body organ, and capable of being engaged by a negative pressure suction force.

It is therefore an object of the present invention to provide a retraction device that allows the indirect manipulation of a beating heart as a whole through the application and maintenance of a tensile load on the non-beating pericardium tissue anatomically attached to beating heart, and where said pericardium tissue is engaged by a negative pressure suction force.

It is another object of the present invention to engage the non-beating pericardium tissue without piercing therethrough and thereby tending to minimize risk of inducing trauma or damage to organs or tissue behind or adjacent the pericardium.

It is a further object of the present invention to attempt to facilitate posterior artery grafts on the beating heart through indirect manipulation of the beating heart, such that the undesirable physiological effects associated with direct contact manipulation of the beating heart might be alleviated or avoided.

It is a further object of the present invention to attempt to position and orient a beating heart as a whole without the necessity of directly contacting the pulsating heart surface and without materially impeding or restricting the natural beating function of the heart, thereby promoting a reduction in the likelihood of producing undesirable physiological effects associated with direct contact manipulation of the beating heart.

It is another object of the present invention to attempt to position and orient the beating heart indirectly through a device acting at a remote location away from the target work-site on said beating heart where the surgical intervention is to be performed.

It is an additional object of the present invention to attempt to apply the concepts and principles of the present invention as they relate to beating heart CABG to other suitable types of surgery which may require retraction of membrane-like body tissue engaged through a negative pressure suction force.

SUMMARY OF THE INVENTION

According to one broad aspect of the present invention, there is provided a surgical apparatus for retraction of tissue, the surgical apparatus comprising a tissue-engaging member for providing on the tissue a negative pressure suction force which is sufficient to retract same, the tissue-engaging member having a deformable skirt for contact with the tissue, the deformable skirt defining a contacting perimeter for substantially air-sealed engagement with the tissue, and wherein a negative pressure plenum is formed within the deformable skirt when the tissue engaging member is operatively connected to a negative pressure source and when the contacting perimeter of the deformable skirt is placed against the tissue in substantially air-sealed engagement therewith.

BRIEF DESCRIPTION OF THE DRAWINGS

For better understanding of the present invention and to show more clearly how it may be carried into effect, reference will now be made by way of illustration and not of limitation to the accompanying drawings, which show an apparatus according to the embodiments of the present invention, and in which:

FIGS. 12A to 12D illustrate several variants of the apex-contacting member of the bracing member according to the fourth embodiment of the present invention illustrated in FIGS. 10 and 11;

DETAILED DESCRIPTION OF THE INVENTION

The features and principles of this invention can be applied, in whole or in part, to other types of cardiac surgery requiring the strategic positioning and orientation of a beating heart as a whole organ. By way of illustration, the description of the embodiments that follows herebelow will however focus on applying the features and principles to beating heart CABG surgery.

In part, the embodiments of this invention may advantageously be applied, if desired, to the surgical retractor and positioning means described in above-referenced copending Canadian patent application Serial No. 2,216,893, the contents of which are incorporated herein by reference. This existing application has been assigned to CORONEO Inc., the assignee of the present application. Alternatively, the embodiments of the invention may also be applied to other types of surgical retractors and other types of positioning means capable of securing the pericardium retraction device according to the present invention in a substantially stable orientation and position relative to the surgical retractor. Alternatively, the surgical retractor may be replaced by other substantially stable surgical platforms that may be engaged with the positioning means to secure the pericardium retraction device according to the present invention. Such surgical platforms would include: a surgical table, a surgical bridge or truss or truss member attached to a surgical table and spanning the patient or set adjacent to the patient, or other like platforms.

Figure 1:
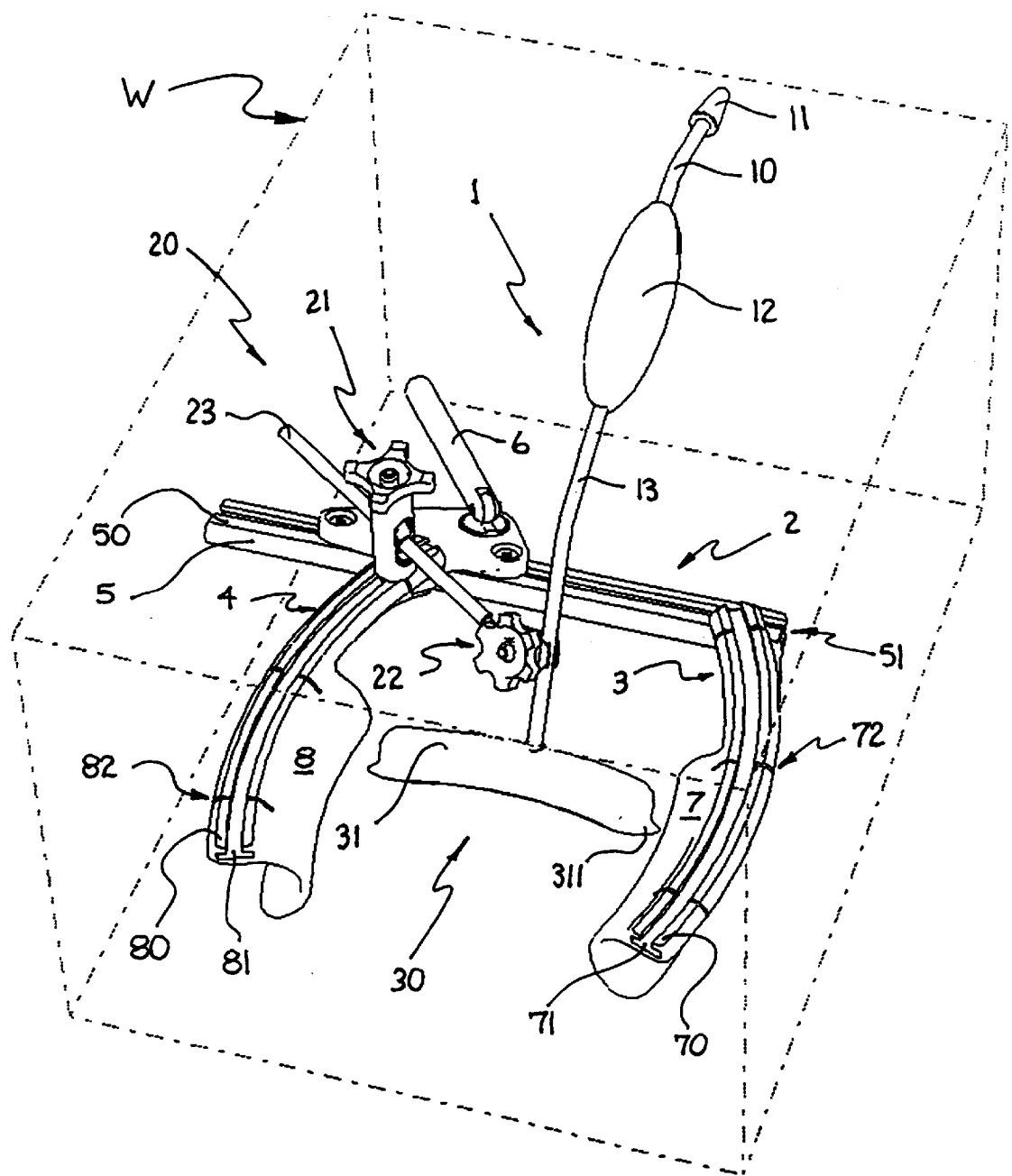
FIG. 1 is a perspective view of a first embodiment according to the present invention illustrating the deployment of a pericardium retraction device oriented and positioned within a surgical workspace by a positioning means attached to a sternum retractor.

During the course of a cardiac surgery, a surgeon needs to perform certain tasks within a surgical workspace (labelled "W" in FIG. 1). This workspace W is defined by an area that contains generally the perimeter of a deployed sternum retractor and a buffer zone therebeyond, with the area extending below generally to the depth of the patient's thorax, and above generally to the height above the retracted chest cavity in which the surgical apparatus is contained and manipulated.

By way of a general overview and with reference to FIG. 1, a surgical apparatus with which the invention may be used is comprised of three main components, a pericardium retraction device 1, a positioning means such as positioning and articulation mechanism 20 and a sternum retractor 2. The sternum retractor 2 is illustrated in its deployed state, thereby creating and maintaining the surgical window that provides the surgeon with access to the patient's internal coronary organs, which include the heart, the pericardium tissue, the aorta and vena cava, the coronary arteries and veins, the pleurae, the thymus, and other anatomical features.

The sternum retractor 2 includes four major parts: (i) an elongated rack bar 5, (ii) a first retractor spreader arm 3 being preferably fixed to the rack bar 5, (iii) a second retractor spreader arm 4 being preferably movable with respect to the rack bar 5, and (iv) an actuator 6 for effecting movement of the retractor spreader arm 4 relative to retractor spreader arm 3.

Retractor spreader arms 3 and 4 extend in a direction substantially transversely with regard to the rack bar 5, generally in the same direction therefrom and in a parallel orientation with respect to one another. The movable arm 4 can be displaced along the rack bar 5, and relative to the other arm 3, preferably through the rotation of the actuator 6 activated by the surgeon. The actuator 6 is operatively connected to the rack bar 5 and to the other spreader arm 4, and is translatable along the length of the rack bar 5. This is preferably achieved by the engagement of a pinion mechanism (not shown) of actuator 6 with the rack teeth on rack bar 5. Two retractor blades 7 and 8 are respectively provided with the retractor spreader arms 3 and 4, preferably disposed below the rack bar 5 when the sternum retractor 2 is deployed on a patient. The retractor blades 7 and 8 engage with and serve to retract a portion of the patient's incised skin, the two halves of the patient's incised sternum and the patient's ribcage thereby exposing the coronary organs to be operated on through the resultant surgical window. When viewing the resultant surgical window from above the patient, the retractor arms 3 and 4 of the deployed sternum retractor 2 each have a generally arcuate orientation.

The sternum retractor 2 advantageously comprises arcuate rails 70 and 80 along the top of arcuate retractor spreader arms 3 and 4, respectively. The rails 70 and 80 configure an inverted T-slot arcuate passage 71 and 81, respectively, preferably centrally located within said rails, and preferably extending throughout the entire arcuate length of said rails. A similar linear longitudinal rail 50, may also be configured along the top of rack bar 5. Longitudinal rail 50 is also configured with an inverted T-slot longitudinal passage 51, preferably extending throughout its entire longitudinal length. These said rails form a mounting perimeter that can advantageously serve to engage a positioning and articulation mechanism 20 that may be utilized to place a variety of mechanical coronary stabilizers during beating heart CABG surgery, for instance, as described in previously mentioned Canadian application Serial No. 2,216,893. Alternatively, the positioning and articulation mechanism 20 may also be utilized to set a pericardium retraction device 1 in a substantially stable position and orientation within the surgical workspace W. As well, these rails can also be utilized to engage other surgical apparatus, that may need to be secured along the perimeter of the sternum retractor 2 during cardiac surgery.

A plurality of slit-like channels 72 and 82 are configured along the arcuate arms 3 and 4 and cut through the arcuate rails 70 and 80, respectively. FIG. 1 illustrates three such slit-like channels 72 on the retractor spreader arm 3 and three such slit-like channels 82 on the retractor spreader arm 4. The slit-like channels 72 and 82 extend downwards from the top of the rails 70 and 80 to a depth preferably below the entire depth of the inverted T-slot arcuate passages 71 and 81, preferably by an amount equivalent to the width of said slit-like channel. The slit-like channels 72 and 82 in the present invention are configured so that a wire-like filament will not restrict or otherwise hinder the functionality of the positioning and articulation mechanism 20 when such mechanism becomes engaged in said passages 71 and 81 of said rails 70 and 80, provided the wire-like filament is placed in the deepest position within said slit-like channel, as is the case in some of the embodiments of the present invention to be described in greater detail below.

Figure 2:
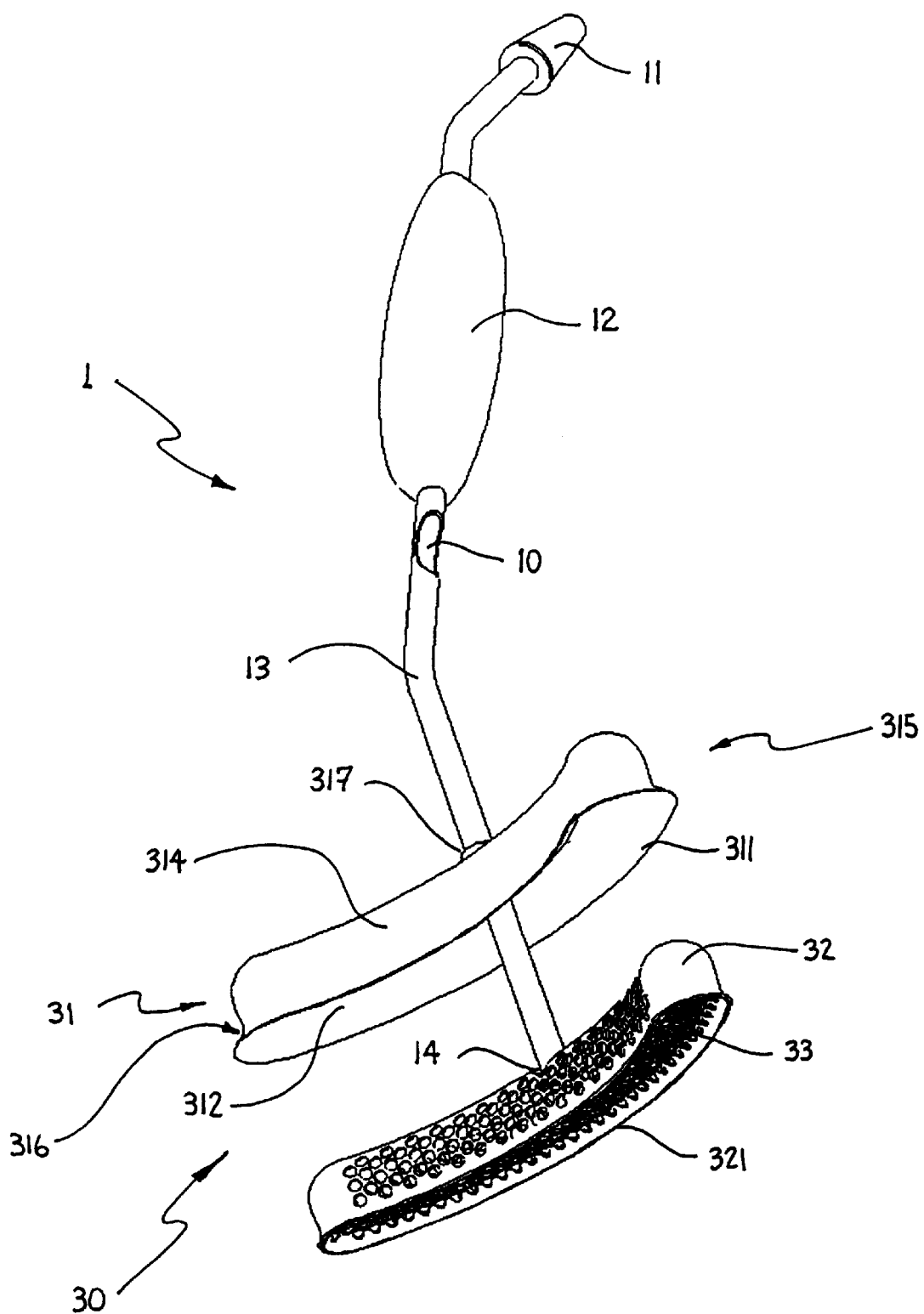
FIG. 2 is a partially dismantled isometric view of the pericardium retraction device illustrated in FIG. 1.

As further illustrated in FIG. 2, the first embodiment of a pericardium retraction device 1 according to the present invention is comprised mainly of a tissue-engaging member 30, a device manipulating means such as shaft member 13, a conduit means such as conduit passage 10, and a suction line interface means such as pneumatic fitting 11. The tissue-engaging member 30 is of a substantially arcuate shape when viewed along the longitudinal axis of shaft member 13. It is further comprised of a substantially-elastic sheath 31 serving as an outer shell that is insertable over a substantially-rigid inner structure 32. Inner structure 32 is substantially air permeable. For instance the inner structure may be designed and produced with an open configuration structure, such as a perforated sheet structure or a truss-like space frame structure. Inner structure 32 is rigidly attached at one side thereof to shaft member 13 in the vicinity of source orifice 14, in either a permanent or demountable assembly. At another side thereof, inner structure 32 is capped by a substantially planar tissue ingestion-limiting means such as ingestion-limiting baffle 33. Ingestion-limiting baffle 33 is also of a substantially rigid and substantially open configuration.

Sheath 31 is configured with a cut-out slot 317 that allows it to slide over pneumatic fitting 11 and shaft member 13, prior to fitting over inner structure 32. The cut-out slot 317 must be sufficient to allow insertion over any protrusions, such as manipulation handle 12 while stretching the elastic sheath 31, if necessary to facilitate insertion.

The proximal end of the shaft member 13 is configured with a pneumatic fitting 11 which will allow hook-up to a negative pressure source, such as commonly available in most operating rooms. In this first embodiment, the shaft member 13 is substantially tubular thereby configuring an integral conduit passage 10 which serves to communicate the proximal pneumatic fitting 11 with the distal tissue-engaging member 30. This tends to result in an unencumbered, more ergonomic surgical workspace W, free from connections to peripheral conduits and equipment that may otherwise be disposed in the vicinity of the surgical intervention site. Alternatively, the conduit passage 10 may be a separate tubular line either housed inside at least a portion of the shaft member 13, or running alongside at least a portion of the said shaft member.

During multiple vessel beating heart CABG, the pericardium sac is incised usually along the anterior surface of the beating heart and along the long axis of the heart. The pericardium tissue is subsequently unraveled from the surface of the beating heart to expose at least a portion of the beating heart that will undergo the bypass graft surgical intervention. More specifically, during coronary artery revascularization of an inferior or posterior artery such as the circumflex artery (Cx), posterior descending artery (PDA), obtuse marginal artery (OM), or postero-lateral artery (PLA), the surgeon or assistant will position the pericardium retraction device 1 in a manner that engages the tissue-engaging perimeter 311 thereof with a portion of the pericardium tissue. During the coronary revascularization of these above mentioned arteries, it is preferable to engage the pericardium retraction device 1 with the side of the pericardium tissue that was in contact with the heart surface prior to the incision of said tissue, and also preferable to engage pericardium retraction device 1 at a location approximately 1.5 inches away from the interface where the pericardium tissue is anatomically attached to the beating heart and the major vessels. A tissue-engaging member 30 with a substantially arcuate shape is advantageous for engaging the pericardium tissue along this said interface.

With suction introduced, a negative pressure plenum is formed by the inside surface 312 of sheath 31 and the top of the pericardium tissue that is engaged within the tissue-engaging perimeter 311 of said sheath. A substantial seal between the outer shell formed by elastic sheath 31 and the top surface of the pericardium tissue along perimeter 311, and another substantial seal between the said sheath and inner structure 32 along cut-out 317, render said negative pressure plenum as non-flowing whereby the airflow through tissue-engaging member 30 is temporarily interrupted by its engagement with the pericardium tissue. The suction force exerted through the tissue-engaging member 30 serves to engage the pericardium tissue, but also to adhere the inner surface 312 of the elastic sheath 31 against the rigid open configuration surfaces of inner structure 32. At least one conduit passage 10 must be in communication with said non-flowing negative pressure plenum to supply suction force to engaged pericardium tissue.

In this first embodiment, elastic sheath 31 may be produced from any suitable polymeric material approved for surgical use. Depending on the polymeric material selected, the elastic sheath 31 may be disposable thereby tending to facilitate the cleaning and sterilization of underlying inner structures 32 and 33 which preferably form a reusable assembly. Alternatively, the elastic sheath 31 may be reusable provided the sheath's polymeric material properties are well-suited to and do not degrade after repeated sterilization cycles. Alternatively, if the polymeric material properties degrade after several sterilization cycles the sheath 31 may be replaced at regular intervals after a certain number of surgeries.

Sheath 31 may be designed to have variable elastic properties throughout its shape either by virtue of its variable thickness or by virtue of its variable composition during fabrication. Reinforcement fibers may also be used in the fabrication of the polymeric sheath 31 to bias its elasticity along certain axes. This is especially beneficial where the inner structure 32 and shaft member 13 are rigid, whereby elastic sheath 31 acts as a buffer in elastic gradient between said rigid members 32 and 13 and non-structural membrane-like pericardium tissue. This buffer in elastic gradient may encourage the membrane-like pericardium tissue to remain in compliant contact with tissue-engaging perimeter 311 of said sheath.

Once sheath 31 is fully assembled over inner structure 32, the tissue-engaging perimeter 311 extends outwardly beyond the inner structure perimeter 321. This flexible and substantially elastic protrusion tends to provide flexibility in the design to cater to different patient anatomies and to assist with some degree of ingestion of the pericardium tissue by the tissue engaging member 31 regardless of variations in anatomy. Ingestion of the pericardium tissue is discussed in greater detail below.

Figure 3A:
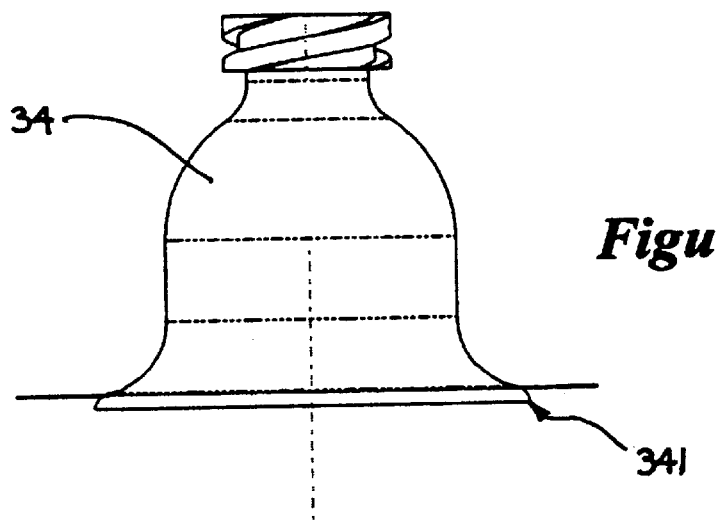
FIGS. 3A to 3C schematically illustrate various dispositions of a deformable skirt means of a pericardium retraction device according to the first embodiment of the present invention comprised of a substantially circular tissue-engaging perimeter.
Figure 3B:
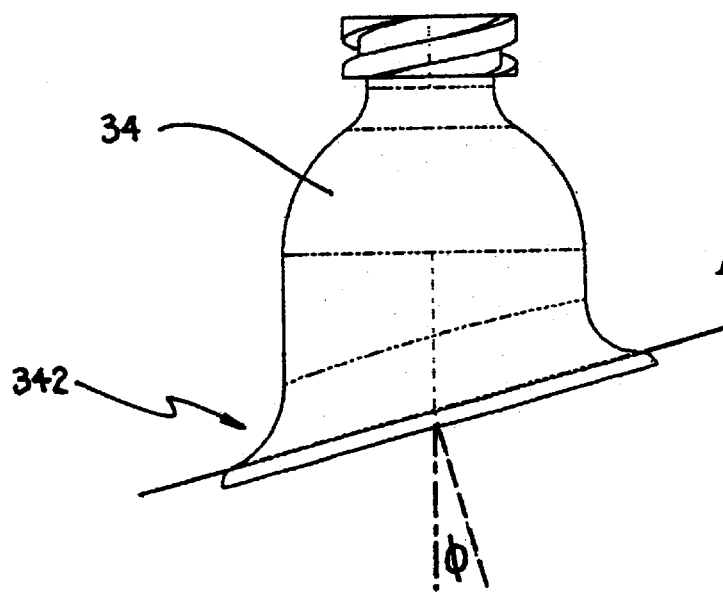
Figure 3C:
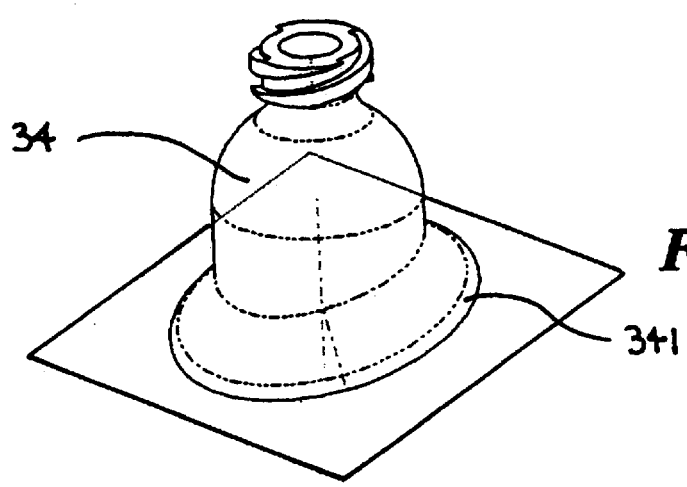
Figure 15:
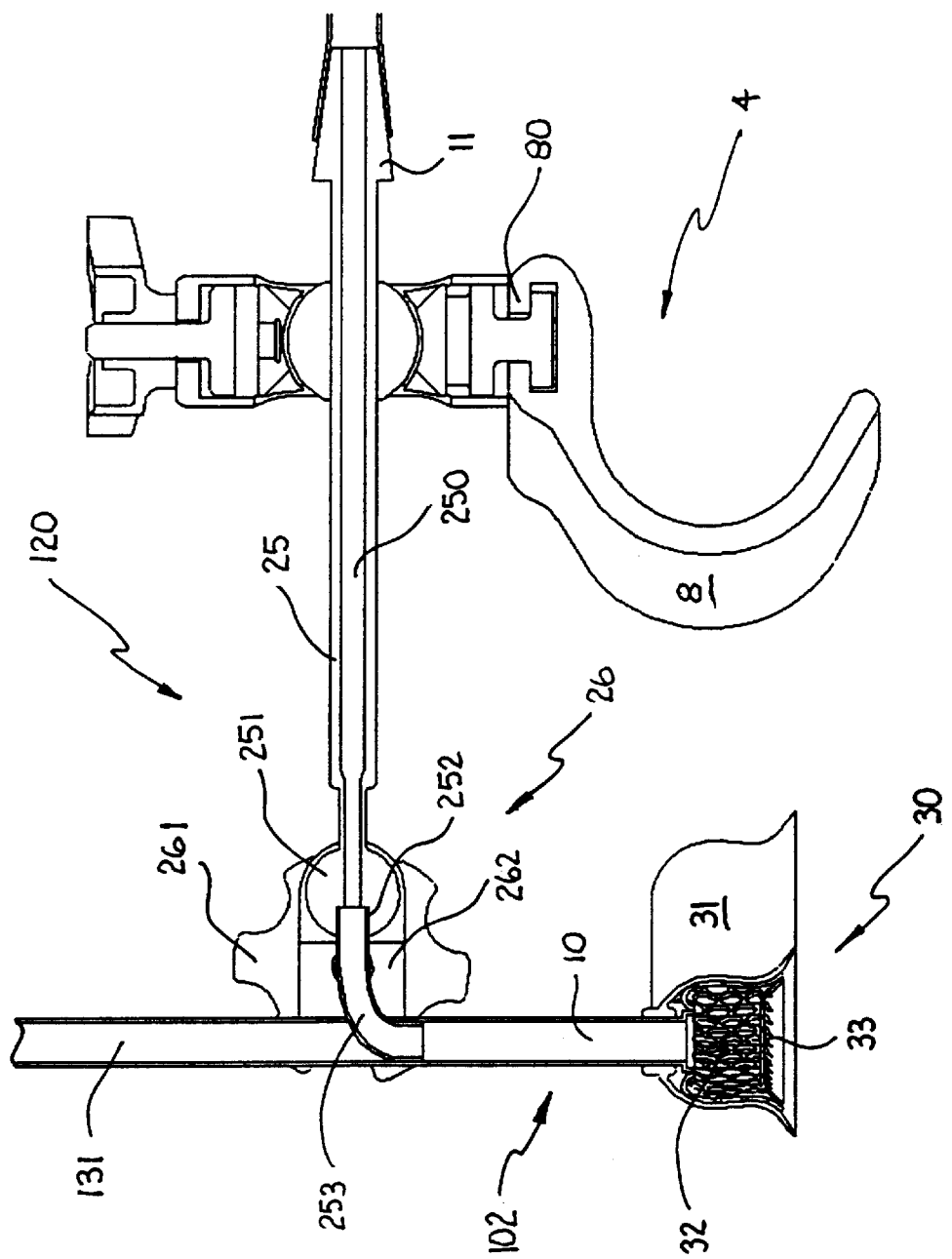
FIG. 15 is a cross-sectional, elevational view of a pericardium retraction device according to a seventh embodiment of the present invention, comprising a conduit means which is provided through a member of the positioning means.

The open area perimeter of sheath 31 is configured with a tapered and beveled terminal edge in the nature of a deformable skirt 316, as best shown in FIGS. 2 and 15. Extending outwardly beyond inner structure perimeter 321, this deformable skirt 316 achieves a substantially compliant seal perimeter at tissue-engaging perimeter 311, capable of engaging the pericardium tissue throughout a range of spatial orientations which the pericardium tissue may assume relative to inner structure 32. The deformable skirt 316 provides readjustment of the substantially planar surface formed by tissue-engaging perimeter 311 depending on the direction of application of tensile retraction loads applied to and reacted by the pericardium tissue. A tensile retraction load applied to the pericardium tissue in a direction substantially parallel to the axis of shaft member 13 distorts the beveled edge of deformable skirt 316 equally around the tissue-engaging perimeter 311, in an inward direction toward the center of said tissue-engaging perimeter 311. If the tensile retraction load is applied to the pericardium tissue in a skewed direction relative to the axis of shaft member 13, the beveled edge of skirt 316 will distort unevenly around the tissue-engaging perimeter 311 in a fashion that the substantially planar surface formed by tissue-engaging perimeter 311 is now oriented substantially perpendicular to the direction of application of said manipulation force or substantially perpendicular to the pericardium reaction force to imposed retraction loads. This is better illustrated in FIGS. 3A–3C, and explained in this case with a single tissue-engaging member such as suction port 34 which has substantially circular tissue-engaging perimeter 341. Apart from the cross-sectional shape of the suction port 34, it generally provides a construction similar to that of tissue engaging member 30. By virtue of the deformable skirt 342, the substantially planar surface formed by tissue engaging perimeter 341 engaged with pericardium tissue may assume a virtually infinite number of spatial orientations. These spatial orientations may be defined by a vector (not shown) that passes through the center of perimeter 341 and is normal to the substantially planar surface formed by said perimeter 341 lying within a substantially conical volume of angle $\phi$ (not shown) relative to the centerline of suction port 34.

The ingestion-limiting baffle 33 illustrated in FIG. 2, ensures that the pericardium tissue will not be entirely ingested within inner structure 32 (if said baffle is not present), but ingested the optimum amount to regulate the suction forces on the engaged pericardium tissue derived from negative pressure acting thereon. Since the source orifice 14 for the negative pressure is typically much smaller in area than the area required to achieve the desired suction force through tissue-engaging member 30, the ingestion-limiting baffle 33 serves to ensure the suction force reacts on a much larger area of pericardium tissue. The structural integrity of the ingestion-limiting baffle 33, combined with the inner structure 32, ensure the structural perimeter 321 remains open to maintain the desired suction force. Furthermore, structural perimeter 321 must remain substantially rigid to keep elastic sheath 31 from rippling along its tissue engaging perimeter 311 due to the effect of the negative pressure suction. This rippling would tend to render more difficult the compliance of the pericardium to the tissue engaging perimeter 311, since such tissue would be required to conform to the irregular shape of the rippled perimeter. The pericardium tissue is partially ingested within tissue-engaging member 30 by an amount substantially equal to the extension of tissue-engaging perimeter 311 of sheath 31 beyond structural perimeter 321 of inner structure 32. The ingested pericardium tissue contacts the ingestion-limiting baffle and assumes a shape conforming to the shape of the said baffle.

The tissue ingestion-limiting baffle 33 preferably forms an integral assembly with the open internal structure 32, whereby it may be demountably assembled with mechanical fasteners or by virtue of a clipped-in assembly, or it may be permanently mounted by gluing, welding, brazing, or other like means along perimeter 321. Alternatively, the tissue ingestion-limiting means may be part of elastic sheath 31, for instance finger-like protrusions extending from inner surface 312 in a direction normal thereto.

Figure 4A:
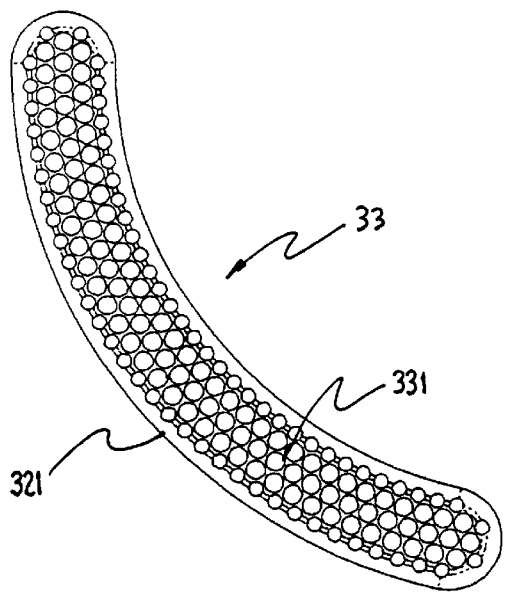
FIGS. 4A to 4D illustrate several variants of a tissue ingestion-limiting means of the pericardium retraction device of the first embodiment of FIGS. 1 and 2.
Figure 4B:
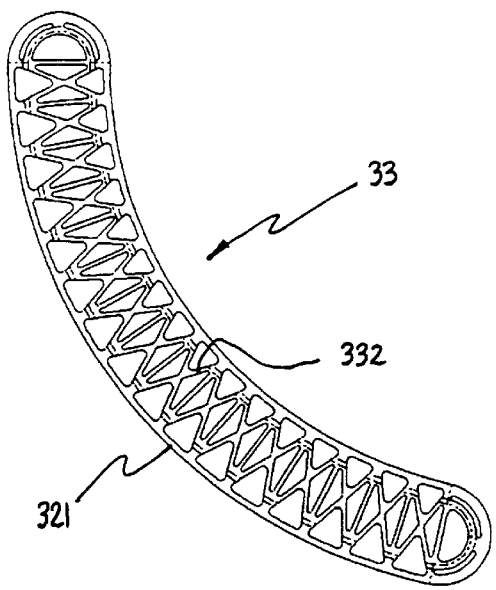
Figure 4C:
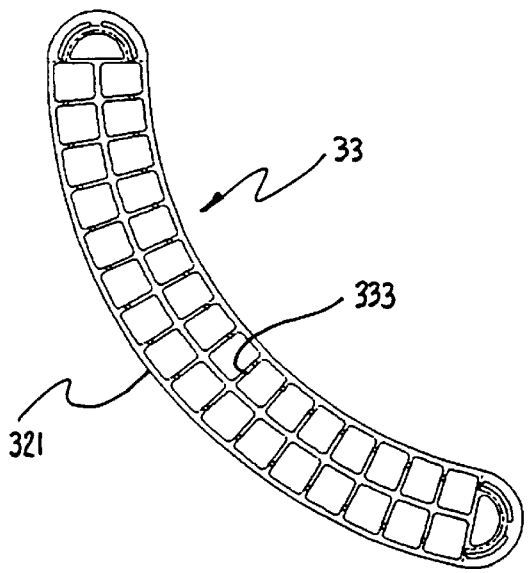
Figure 4D:
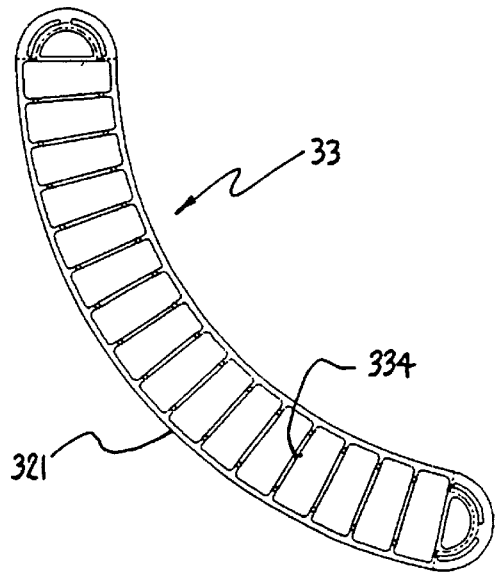

Variations in the open configuration of ingestion-limiting baffle 33 are illustrated in FIGS. 4A–4D. FIG. 4A illustrates an ingestion-limiting baffle with substantially circular perforations 331, FIG. 4B illustrates a baffle with webs defined by substantially triangular perforations 332, FIG. 4C illustrates a baffle with webs defined by substantially square perforations 333, and FIG. 4D a baffle with webs defined by substantially rectangular perforations 334. Other like open configurations for the tissue-ingestion baffle are possible without departing from the spirit of the present invention. As those skilled in this art will appreciate, the resulting suction force on the engaged pericardium is partly a function of the open area through baffle 33 based on its perforation density.

The substantially open configuration inner structure 32 may be configured with the same variations in construction as the tissue ingestion-limiting baffle 33; that is, webs defined from a variety of perforations.

The shaft member 13 is may comprise a manipulation handle 12 for the surgeon to manipulate, orient, and position the pericardium retraction device 1. The desired verticalization of the beating heart is achieved by the application of a tensile load to the pericardium tissue by the surgeon's manipulation of the pericardium retraction device 1 that is engaged with a portion of pericardium tissue by virtue of a negative pressure suction force. Heart verticalization is achieved in an indirect manner whereby the beating heart is not in direct contact with the enabling surgical apparatus in the nature of a pericardium retraction device. Moreover, the pericardium retraction loads tend not to impose any considerable restriction on the beating function of the heart thereby increasing the likelihood of achieving hemodynamically stable beating heart manipulations.

The desired pericardium retraction load or the desired heart verticalization is maintained by securing the pericardium retraction device 1 to the sternum retractor 2 through the positioning and articulation mechanism 20. The positioning and articulation mechanism 20 is preferably comprised of a first joining member such as a first articulation member in the nature of a cylindrical post 21 and a second joining member such as a second articulation member in the nature of a spherical clamp 22, each capable of providing a multitude of motion degrees of freedom. Shaft member 13 is inserted in between the clamping members of spherical clamp 22. The clamping members may engage the shaft member 13 anywhere along its longitudinal length. Final adjustments to the pericardium retraction load may also occur with the shaft member 13 engaged between clamping members of spherical clamp 22 before the entire positioning and articulation mechanism 20 assembly is rigidly secured through the action of each of the tensioning knobs of spherical clamp 22 and cylindrical post 21.

In-process readjustments to the pericardium retraction load may also occur by loosening one or both of each said tensioning knobs, and not disengaging the pericardium retraction device 1 from the spherical clamp 22. With the tensioning knob of spherical clamp 22 slightly loosened, the pericardium retraction device 1 is free to translate through the clamping members of spherical clamp 22, rotate about the axis of shaft means 13, pivot about axis of rod 23, and articulate angularly within a plane formed by the centerlines of articulation rod 23 and shaft member 13. With the tensioning knob of cylindrical post 21 loosened, articulation rod 23 is free to rotate about its longitudinal axis, is free to translate through the cylindrical post 21 in a direction along its longitudinal axis, is free to articulate into and out of the retracted chest cavity by increasing or decreasing the angle between its longitudinal axis and the centerline axis of cylindrical post 21, is free to rotate about the centerline axis cylindrical post 21, and is free to slide within arcuate passage 81 (or either of the arcuate passages 71 and 51).

These motion degrees of freedom provide the mechanical flexibility to tailor the surgical set-up to distinct patient anatomies tending to result in an ergonomic deployment of the pericardium retraction device. Cylindrical post 21 is preferably already installed with the first articulation rod 23 on the perimeter rail 80 (or perimeter rails 70 or 50) of sternum retractor 2 prior to engaging the pericardium tissue with the pericardium retraction device 1. The positioning and articulation mechanism 20 serves to set the pericardium retraction device 1, in virtually any substantially stable position and orientation within surgical workspace W and relative to a sternum retractor 2. A suitable positioning and articulation mechanism which may advantageously be used with the pericardium retraction device of the present invention is disclosed in the above-mentioned Canadian patent application Serial No. 2,216,893, whose specification is incorporated herein by reference.

In this first embodiment, the tissue-engaging member 30 forms an arcuate opening for engaging the pericardium tissue. Alternatively, the tissue-engaging perimeter 311 can be configured on the front face 314 of elastic sheath 31, the rear face 315, or any combination thereof.

Shaft member 13 is rigidly attached to the top portion of inner structure 32 in preferably a substantially perpendicular orientation relative to a plane containing the arcuate spine defining said inner structure 32. Alternatively, the orientation of shaft member 13 relative to inner structure may be varied to include other orientations. As well, a hinge joint or spherical joint may be configured at the junction between shaft member 13 and inner structure 32 to result in a variable angle orientation between said components 13 and 32 depending on direction of the application of the pericardium retraction force applied by the surgeon.

In this first embodiment, the inner structure 32 and shaft means 13 are manufactured from reusable, sterilizable materials approved for use in surgery, in rigid configurations. These include, but are not limited to, stainless steel, aluminum, nickel, or titanium. Alternatively, the inner structure 32 can be designed with stiffness gradient along its defining parameters. For instance, the inner structure can be designed with a variable stiffness along its spine arcuate length in order to tend to more closely comply to the deformed shape of the retracted pericardium tissue. For instance, such a variable stiffness may be defined such that the opposed terminal ends of the inner structure 32 are less stiff than the portions thereof which are adjacent shaft member 13. This can be achieved through selective geometry, varying density of perforations, variable wall thickness, or by anisotropic material properties, as is achieved in variable composition polymers. Alternatively, this first embodiment may also be a reusable, one piece construction, whereby sheath 31 and inner structure 32 are replaced by a structural outer skin. The ingestion-limiting baffle 33 is in this case mounted in a recessed position within structural outer skin with respect to the tissue-engaging perimeter 311.

In broad terms, the surgical procedure for the set-up and deployment of the pericardium retraction device 1 during a beating heart CABG surgery, and relating to the present invention consists of:

(a) performing a full or partial midline sternotomy incision;

(b) cauterizing of any bleeding vessels subsequent to the sternotomy incision;

(c) if an internal thoracic artery (ITA) will be used as a bypass conduit, retracting the two halves of the patient's incised sternum with a surgical retractor suitable for exposing the ITA and the surgical harvesting thereof;

(d) retrieving the surgical retractor used for ITA harvesting, and inserting blades 7 and 8 of sternum retractor 2 along the sternotomy incision;

(e) retracting the patient's ribcage to expose the underlying mediastinum and pericardium tissue;

(f) incising the pericardium sac to expose at least a portion of the patient's beating heart requiring the bypass graft;

(g) deploying the pericardium retraction device 1 by bringing into proximity and in substantial contact with the pericardium tissue (labelled PCT in FIG. 10) the tissue-engaging member 30;

(h) introducing a negative pressure suction through pericardium retraction device 1;

(i) ensuring that a portion of the pericardium tissue is properly ingested within tissue-engaging member 30 and that adequate sealing of negative pressure occurs at the perimeter 311 of said member 30;

(j) while grasping handle 12, spatially orienting and positioning the pericardium retraction device 1, with engaged portion of pericardium tissue within its member 30, in a manner to apply a tensile load on the pericardium tissue and thereby simultaneously positioning and orienting the beating heart anatomically attached to said pericardium tissue;

(k) maintaining the desired beating heart position and orientation by securing the pericardium retraction device 1 to sternum retractor 2 through positioning and articulation mechanism 20, resulting in the desired access to the coronary artery bed requiring the bypass graft;

(l) to perform bypass grafts on the inferior or posterior coronary artery beds, preferably placing the beating heart in a verticalized position with the longitudinal axis of the heart assuming a substantially vertical orientation through the rotation of the apex of the heart relative to the base of the heart outwardly through the retracted ribcage;

(m) with the beating heart in the desired position and orientation to improve surgical access to target coronary artery, deploying a positioning and articulation mechanism 20 and associated mechanical coronary stabilizer according to the above-mentioned copending Canadian patent application Serial No. 2,216,893, or other like positioning and heart contacting means that allow the surgeon to perform a bypass graft on the beating heart;

(n) disengaging the mechanical coronary stabilizer, or other like means, from the surface of the beating heart after the completion of the bypass graft;

(o) disengaging the pericardium retraction device 1 from its positioning and articulation mechanism 20 and easing the beating heart back to its natural position into the chest cavity through the reduction of the tensile load applied through the pericardium retraction device 1;

(p) turning off the negative pressure suction through the pericardium retraction device 1 and retrieving said device 1 from retracted chest cavity;

(q) Closing retractor arms 3 and 4 and retrieving sternum retractor 2;

(r) Closing the midline sternotomy surgical incision.

The embodiments of the pericardium retraction device that follow and described in more detail below, are deployed and set up in a similar surgical procedure as described above, provided the pericardium tissue is engaged by virtue of a negative pressure suction force.

Figure 5:
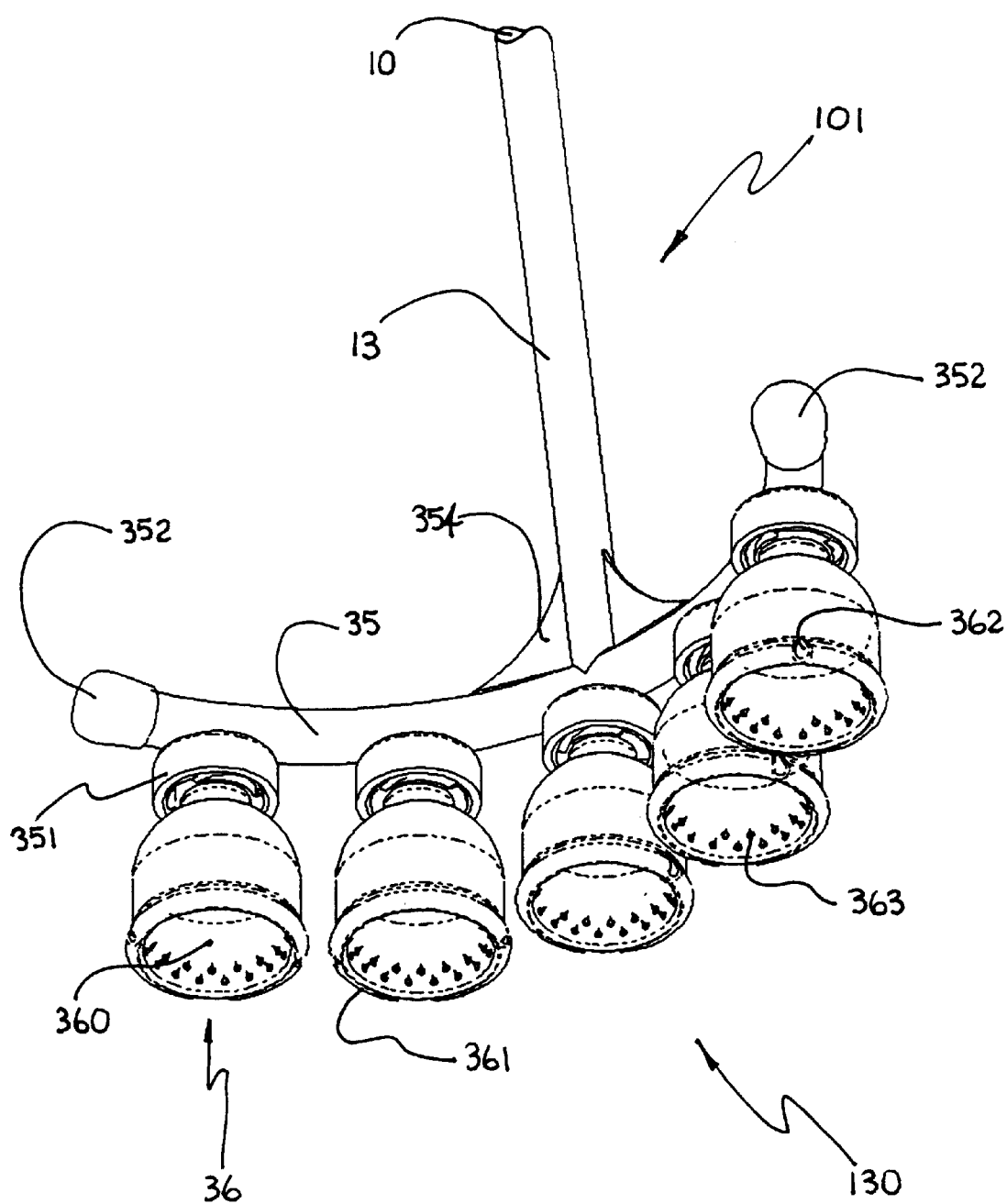
FIG. 5 is a perspective view of a pericardium retraction device according to a second embodiment of the present invention comprised of a plurality of tissue engaging members in the form of suction ports.
Figure 6:
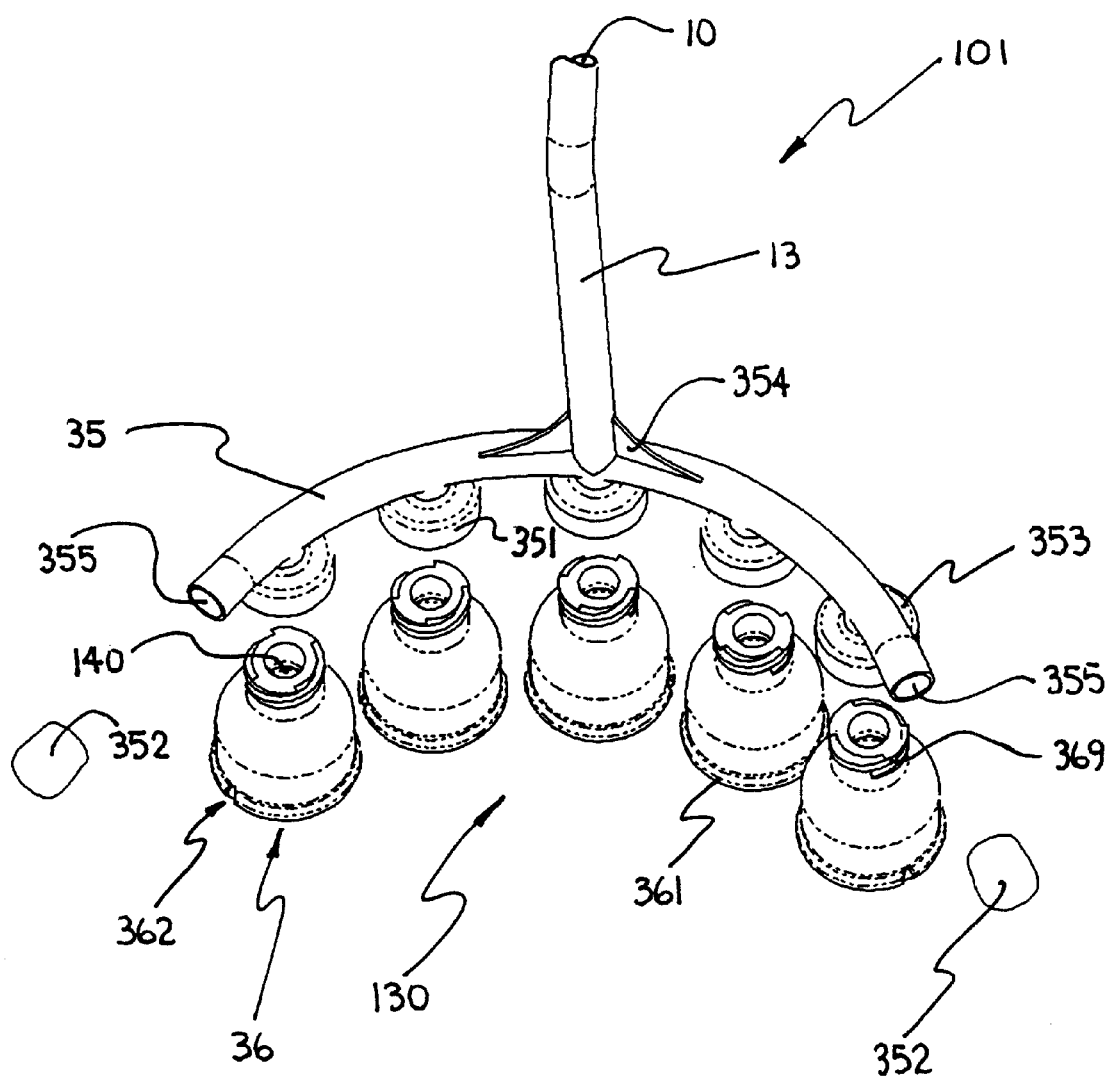
FIG. 6 is an exploded view of the pericardium retraction device according to the second embodiment of the present invention illustrated in FIG. 5.
Figure 7:
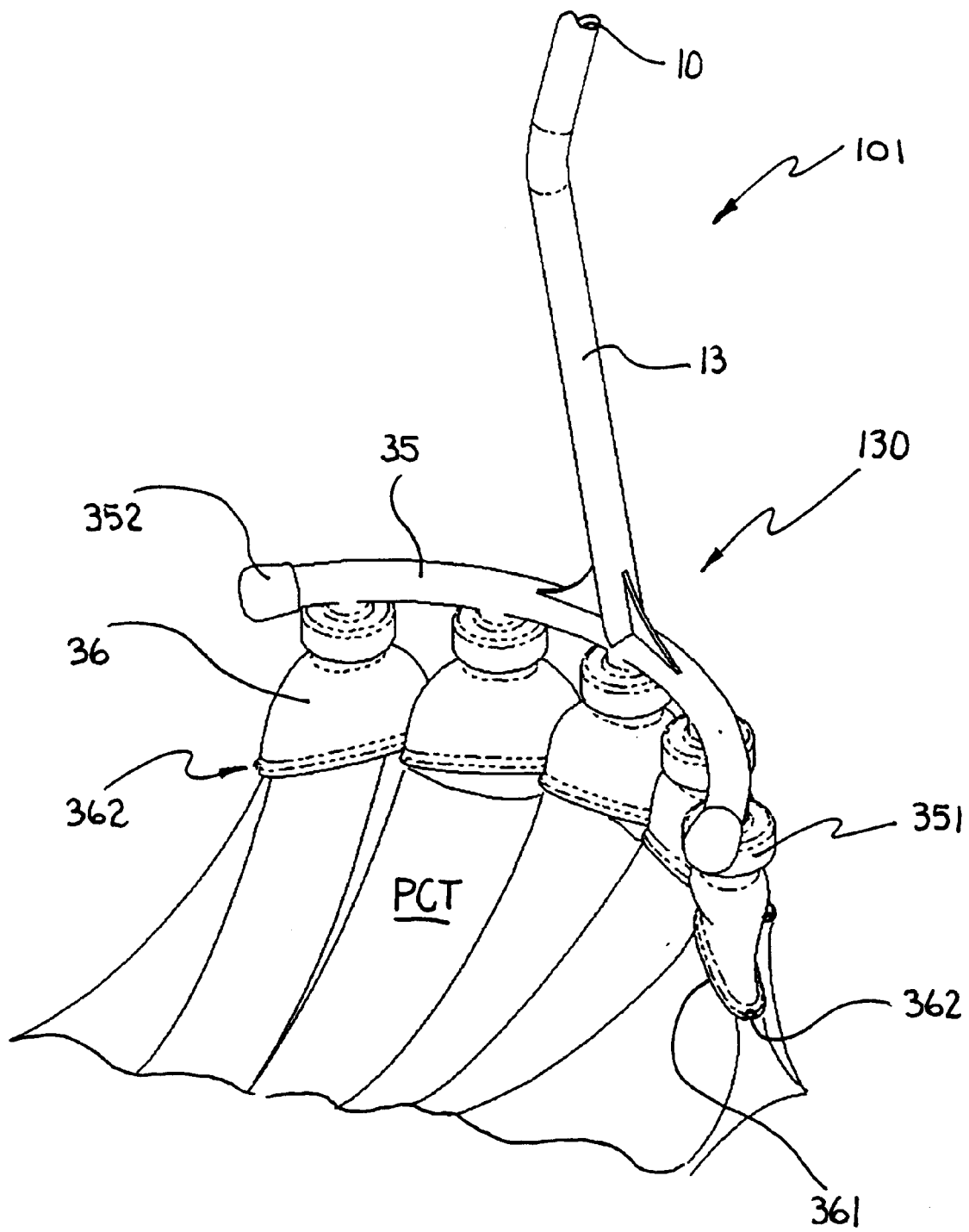
FIG. 7 is a perspective view of the pericardium retraction device according to the second embodiment of the present invention shown in FIG. 5 illustrating the engagement of the pericardium retraction device with pericardium tissue.

FIGS. 5 to 7 illustrate a second embodiment according to the present invention. The tissue-engaging member 130 of the pericardium retraction device 101 is comprised of a plurality of bell-shaped suction ports 36, each demountably attached to a substantially semicircular tubular spine 35 through an attachment fitting 351. This embodiment illustrates five such ports, which shall be referred to as ports A, B, C, D, and E in a clockwise direction. The suction ports 36 are described in greater detail below. The fittings 351 are preferably arranged such that their centerlines are substantially parallel to the centerline defining the semicircular tubular spine 35. Alternative embodiments may have attachment fittings 351, and consequently suction ports 36, attached to spine 35 in a variety of orientations or combination of orientations. For example, ports A, C, and E may be configured with centerlines substantially parallel to the centerline defining semicircular spine 35, and ports B and D may be configured with centerlines substantially perpendicular to the centerlines of ports A, C, and E whereby said ports extend radially outward away from the center of semicircular spine 35.

Conduit passage 10 serves to communicate the negative pressure suction from a pneumatic fitting 11 at the proximal end of the pericardium retraction device 101 to the arcuate manifold passage 355 (FIG. 6) within semicircular tubular spine 35. Semicircular spine 35 serves as a manifold to communicate the negative pressure suction to each of the suction ports 36 through a series of inlet orifices in each of the attachment fitting 351. Orifice 140 through each of the suction ports 36 comes into sealed contact with the inlet orifice in attachment fitting 351 when said suction port 36 engages said spine 35 through said fitting 351.

Spine 35 is attached to the distal end of shaft member 13. Gusset plates 354 or the like may serve to reinforce the structural joint between spine 35 and shaft member 13. One attachment fitting 351 is positioned in line with the centerline of shaft member 13 in order to facilitate cleaning prior to sterilization of the integral conduit passage 10 within shaft member 13. Endplugs 352 are also provided at the arc ends of spine 35 to facilitate cleaning prior to sterilization of the arcuate manifold passage 355. The suction ports 36 are preferably manufactured from an elastic polymeric material, safe for surgical use. If the polymeric material is not suitable for repeated sterilization cycles, the suction ports 36 will be disposable elements and hence the need for a demountable assembly to rigid spine 35. Alternatively, if entire pericardium retraction device 101 is made to be disposable, the interface between the suction ports 36 and spine 35 may be a permanent junction.

Each of the attachment fittings 351 is embodied with an attachment feature 353, in this case an internal double start thread, which interfaces with the attachment feature 369 on suction port 36, in this case an external double start thread (FIG. 6). Alternative attachment features to secure suction ports 36 to the spine 35 may include: a snap-in ridge-in-groove arrangement, a retaining ring, a spring detent feature engaging a retention groove, a flanged suction port laterally engaging a groove feature (tongue and groove arrangement), a hinged clamping flange, a partial-turn drum cam interface, and a "peel and expose" temporary adhesive. This latter "peel and expose" temporary adhesive may be such that it degenerates during post-surgery sterilization cycle, thereby releasing the used suction port 36 from attachment fitting 351 ready to receive a new pre-packaged, pre-sterilized suction port 36 with also with a said "peel and expose" adhesive.

FIG. 7 illustrates the tissue-engaging member 130 with the plurality of deformable suction ports 36 in their deployed shape after each has engaged a portion of the pericardium tissue. Each of the deformable suction ports 36 is comprised of an orifice 140, an attachment feature 369, a tissue-grasping means 363, a tissue-engaging perimeter 361, and at least one deformation bias 362 disposed preferably along said perimeter 361.

In deploying the pericardium retraction device 101 according to this second embodiment, while the negative pressure suction is introduced through the pericardium retraction device, the surgeon first contacts a portion of pericardium tissue with the engaging perimeter 361 of each of the suction ports 36. A substantial seal results about said perimeter 361 of each of the suction ports. A portion of pericardium tissue is ingested within the inside surface of each of the suction ports 36. The seal formed at the perimeter 361 of each suction port 36 and the resultant suction force on the engaged pericardium tissue within each said perimeter, causes the deformable suction port 36 to deform along its bias 362. Folding of suction port 36 along the bias 362 (or the collapsing of the opposing suction port 36 internal surfaces substantially towards one another) sets the tissue-grasping means 363 on inside surface 360 in contact with the ingested pericardium tissue. The deformation bias 362 may be a notch (FIGS. 8A through 8D) or other like means which will promote a localized folding action and resulting partial collapse of the sidewalls of the suction port 36 when such sidewalls are subjected to radial loading due to the effect of suction.

As the surgeon manipulates the retraction device 101 to position and orient the beating heart, the tensile load on the pericardium tissue increases due to the imposed retraction loads. Any expelling action of the engaged portion of pericardium tissue by virtue of the increasing retraction loads on the pericardium tissue, will engage the tissue-grasping means 363 deeper into the portion of ingested pericardium tissue. Consequently, the retraction of the pericardium tissue may be provided through a combination of negative pressure suction force and a resulting mechanical grasping occurring between the inside surface 360 of suction port 36 and ingested pericardium tissue by virtue of the grasping means 363. The tissue-grasping means 363 therefore may be capable of maintaining at least a limited retraction load if the negative pressure suction force is temporarily interrupted or disabled. If it is desired to promote this effect of mechanical grasping in the absence of a negative pressure suction force, the tissue grasping means are preferably in the form of protrusions which extend generally radially towards the center of the engaging perimeter 361 and more preferably, also generally away from the direction in which the pericardium tissue will retract if the tensile load placed thereon is released. In this manner, continued engagement of the grasping means may be promoted when a tensile load is maintained on the pericardium tissue, even in the event that the suction force acting thereon may be temporarily interrupted or disabled. However, once the tensile load is relieved, for instance by a surgeon manipulating the pericardium retraction device in a direction towards the patient's thoracic cavity, it is expected that the tissue grasping means will thereafter disengage from the pericardium tissue once the suction force is absent. Tissue grasping means in the form of protrusions are described below with reference to FIG. 8A. Other tissue grasping means are described below with reference to FIGS. 8B to 8D.

The negative pressure suction force is therefore in a sense the catalyst for inducing the engagement of tissue-grasping means 363 with ingested pericardium tissue within suction port 36. The pericardium retraction device 101 is positioned and secured within the surgical workspace W through the positioning and articulation mechanism 20 and the sternum retractor 2 in the same manner as the first embodiment. When the surgical intervention on the "verticalized" beating heart is completed, the pericardium retraction device 101 is displaced from its retraction-inducing setting to a position within the surgical workspace that relieves the tensile load on the pericardium tissue, thereby also displacing the beating heart to its natural position within the chest cavity. When the negative pressure suction is turned off and the tensile load on the pericardium tissue is relieved, the deformable suction port 31 resumes its original free state, the tissue-grasping means 363 substantially disengages pericardium tissue, and the pericardium retraction device may be retrieved.

Figure 8A:
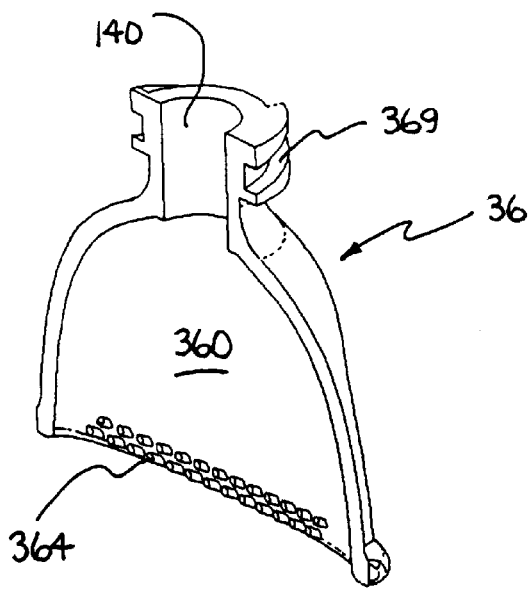
FIGS. 8A to 8D illustrate several variants of tissue-grasping means of the tissue-engaging member of the second embodiment of FIG. 5.
Figure 8B:
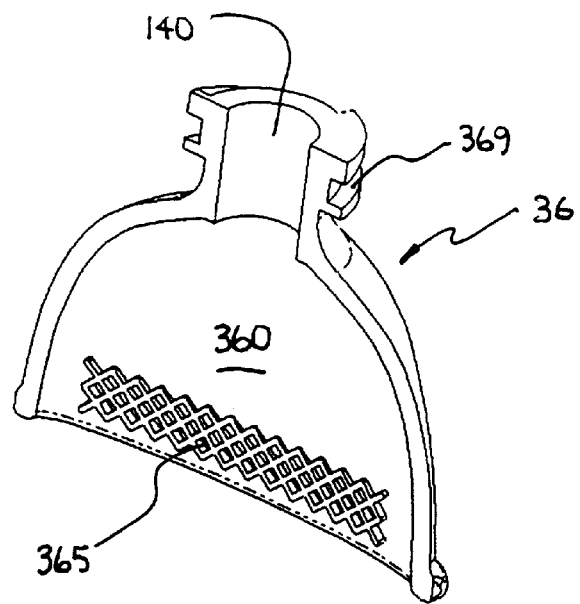
Figure 8C:
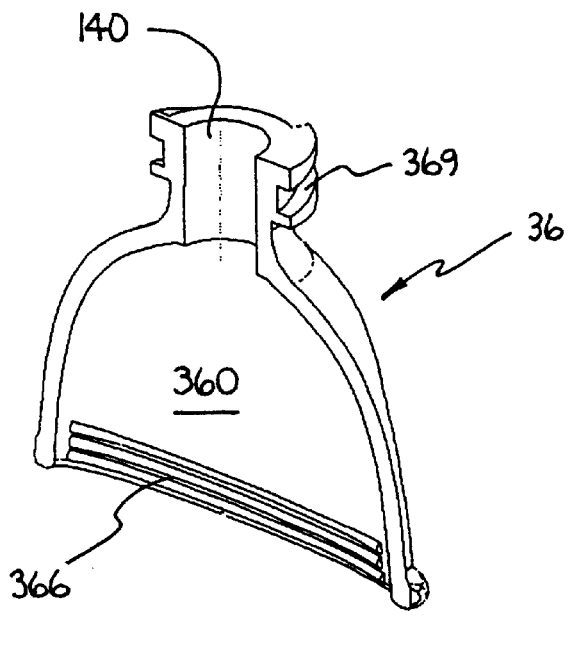
Figure 8D:
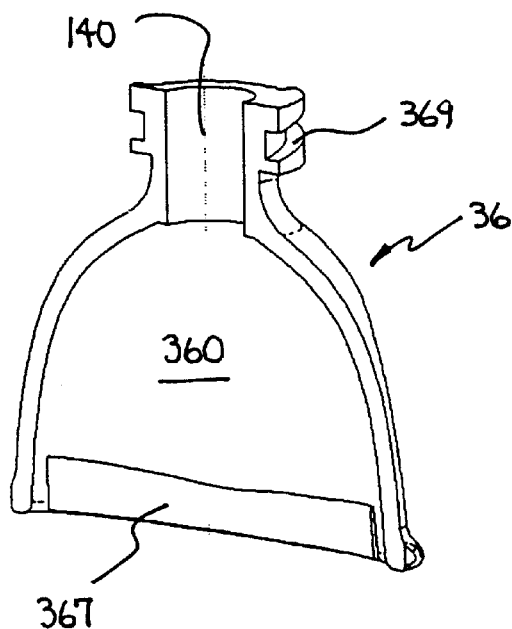

The tissue-grasping means 363 is disposed along at least a portion of the inside surface 360 of the suction port 36, preferably along portions of said inside surface which will be brought into opposition when suction port 36 deforms according to its bias 362. The tissue-grasping means 363 is a surface treatment which promotes its adherence to the ingested pericardium tissue. Several variants of the tissue-grasping means 363 are possible. FIG. 8A illustrates a tissue-grasping means comprised of pedestal-like or pin-like protrusions 364; FIG. 8B illustrates a tissue-grasping means comprised of a grid-like matrix 365; FIG. 8C illustrates a tissue-grasping means comprised of a ridged formation such as a step-like or groove-like perimeter 366; and FIG. 8D illustrates a tissue-grasping means comprised of a tissue adhesive-like coating or layer 367, for instance a hydrogel coating.

The tissue-grasping means 363 may be a resultant feature from the manufacturing process which produces suction port 36. Alternatively, the tissue-grasping means may be or a feature that is introduced during a subsequent fabrication process, such as during assembly injection molding. For example, the tissue-grasping means may be injection molded onto the surface 360 subsequent to the injection molding of suction port 36. Alternatively, the tissue-grasping means may be a separate distinct feature-part, permanently attached or demountably attached to inside surface 360 of suction port 36. For example, a separate flexible metal foil layer glued on the inside surface 360 of suction port 36, protruding metal pins embedded into inside surface 360 of suction port 36.

Other variations of the second embodiment without departing from the spirit of the present invention are possible. Alternatively, instead of a manifold arrangement, each suction port 36 may be fed by its own designated conduit passage 10.

Alternatively, the pneumatic fitting 11 may be incorporated with spine 35 at one of the arc end locations thereby replacing one of the end fittings 352.

Alternatively, the semicircular tubular spine 35 may be of a substantially linear shape or a substantially S-shaped inflected curve shape.

The suction port 36 may be produced from a polymeric material with variable composition and elasticity in at least a portion of its shape, in order to cater its material properties to the desired function at that specific location. For example, a suction port 36 may be produced with substantially rigid attachment feature 369 and substantially rigid protrusions defining its tissue-grasping means 363, but with substantially flexible and compliant tissue-engaging perimeter 361.

Alternatively, suction port 36 may have more than one bias 362 along its perimeter 361 encouraging the desired deformed shape of suction port 36 that will set the tissue-grasping means 363 in contact with the ingested pericardium tissue.

Alternatively, the shape of the contacting perimeter 361 may be substantially oval, substantially lens shaped, or substantially circular. Other shapes for the contacting perimeter 361 may also be suitable, as those skilled in this art will appreciate.

Figure 9A:
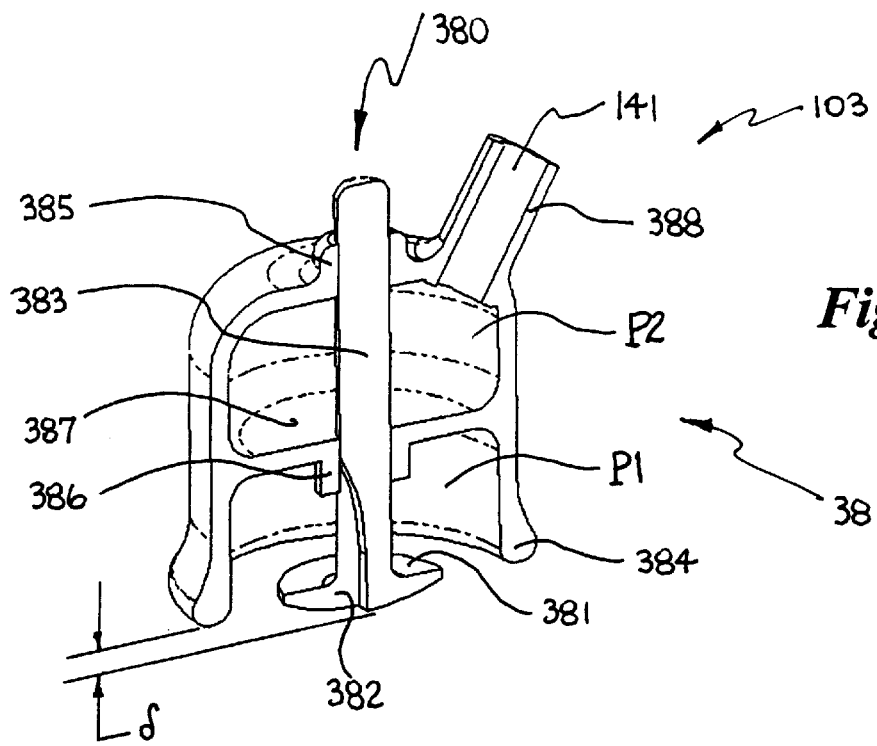
FIG. 9A is a perspective, cross-sectional view illustrating a pericardium retraction device according to a third embodiment of the present invention comprising a valve means shown in a closed, non-deployed state.
Figure 9B:
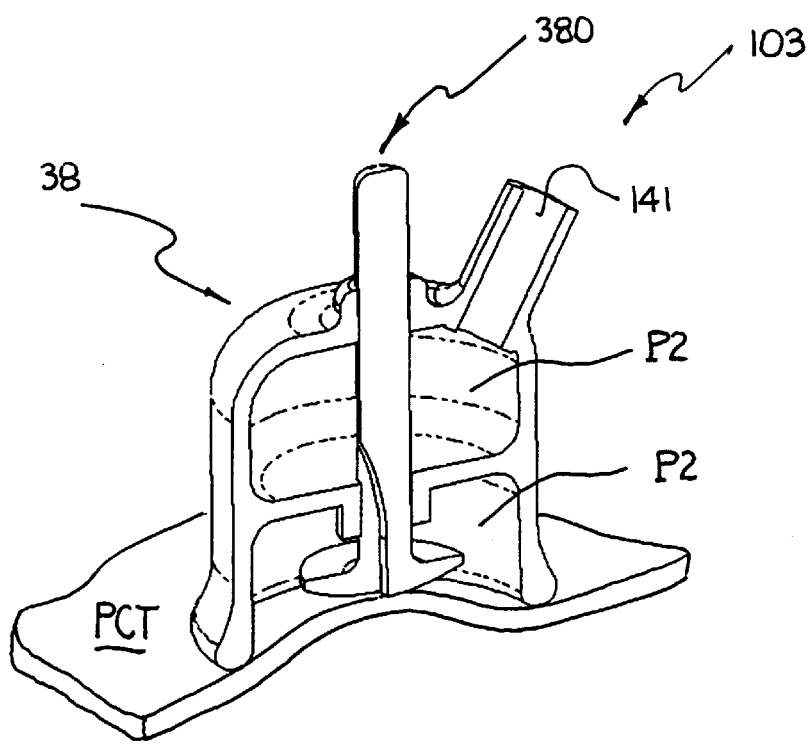
FIG. 9B is a perspective, cross-sectional view illustrating a pericardium retraction device according to the third embodiment of FIG. 9A with the valve means shown in an open, deployed state.

FIGS. 9A and 9B illustrates a third embodiment according to the present invention. The third embodiment comprises, through the provision of a valve means 380, a substantially self-sealing tissue-engaging member 38 such that the flow through the pericardium retraction device 103 is substantially zero even if the negative pressure plenum is not completed by the pericardium tissue in contact with the perimeter 384, as is the requirement in the previous embodiments.

This is advantageous in pericardium retraction devices comprised of a plurality of tissue-engaging members, when not all tissue-engaging members or suction ports are, or can be, in sealing contact with the pericardium tissue. Without a valve means 380, the excessive flow through a non sealing suction port would tend to render ineffective the remaining suction ports as well, due to the inability to generate the desired negative pressure and consequently suction force. Alternatively to incorporating a valve means, this problem can be alleviated by incorporating a designated conduit means 10 for each suction port. This tends to result in a more complex, part-intensive, and consequently more costly apparatus.

In this third embodiment, the tissue-engaging member 38 is comprised of a hollow attachment feature 388, a source orifice 141, a diaphragm member 387, and a spool valve means 380. The hollow attachment feature 388 serves to fixture said tissue-engaging member 38 to a substantially rigid tubular spine (like 35) in a plurality arrangement, or directly to a shaft member 13 in a single port arrangement. The source orifice 141 serves to communicate with the negative pressure source P2 through tubular spine (like 35) and conduit member 10. The diaphragm member 387 delimits a negative pressure plenum within tissue-engaging member 38.

The spool valve means 380 may assume either a "valve closed" position in which the negative pressure plenum P2 is delimited by diaphragm member 387, as illustrated in FIG. 9A, or an "open valve" position in which the negative pressure plenum is delimited by the engaged pericardium along perimeter 384, and as illustrated in FIG. 9B, the substantially ambient pressure P1 drops to negative source pressure P2.

The top surface of tissue-engaging member 38 and the diaphragm member 387 each are provided with a guiding and sealing bore feature 385 and 386 respectively, which serve to guide the spool valve means 380 throughout its travel within the tissue-engaging member 38, and also provide a substantial seal with the shaft 383.

Valve means 380 is comprised of a dish-like plunger 381 which has a slot-like feature 382 to communicate plenum P2 with plenum P1 when shaft 383 is plunged by the engagement of pericardium tissue around perimeter 384. When the pericardium tissue is not in contact with plunger 381, the valve means 380 assumes a stable position within the tissue-engaging member 38 due to a pressure balance, whereby top edge slot-like feature 382 is just cutting off flow through the diaphragm member 387. At the "valve closed" position, the plunger 381 is substantially proud (by a distance δ) from the tissue-engaging perimeter 384, and ready to engage the pericardium tissue.

Plunger 381 is configured with a dish-like shape in order to easily contact the pericardium tissue in a non-traumatic manner, but other shapes are also possible without departing from spirit of the invention. In the "valve open" position, with the plunger 381 at its topmost position within tissue-engaging member 38, plunger 381 also acts as a tissue ingestion-limiting means.

A stopper feature (not shown) to limit the translation of valve means 380 within tissue-engaging member 38 may also be incorporated. Stopper features may include, a stepped diameter, a key-way feature, a transverse dowel, a retaining ring, and other like limit means disposed at the terminal end of the valve means 380 which is opposite the plunger 381 thereof and adjacent sealing bore 385.

A spring member (not shown) may also be incorporated to further encourage valve means 380 to remain in the non-flowing closed position. Initially, this spring load exerted by this said spring member must be overcome by the action of engaging pericardium tissue to plunge open the valve means 380. This said spring load must also be overcome throughout the deployment of the pericardium retraction device 103 by the resultant suction force acting on the engaged pericardium tissue.

Alternatively, instead of mechanical actuation of valve means 380 through the travel of plunger 381, the valve means may be electronically actuated by a proximity sensor which senses the position of the underlying pericardium tissue when said tissue is in proximity to tissue-engaging member 38. The proximity sensor may be designed utilizing a light source, an electromagnetic field, or a heat measurement transducer, to name a few examples.

Alternatively, the concepts of this third embodiment can also be applied to other tissue-engaging members that engage other types of coronary tissue or body tissues in general, and are not limited to engaging pericardium tissue.

The fourth embodiment according to the present invention, introduces an organ bracing member such as a heart apex-bracing mechanism 90, which may be deployed in conjunction with a pericardium retraction device 100. The "verticalized" beating heart (labelled VBH in FIG. 10) and the pericardium tissue (labelled PCT in FIG. 10) anatomically attached to said beating heart are illustrated engaged with the apex-bracing mechanism 90 and the pericardium retraction device 100, respectively. The pericardium retraction device 100 according to the present invention is comprised mainly of a tissue-engaging member 30, a device manipulating means such as shaft member 113, a conduit means such as conduit passage 110, and a suction line interface means such as pneumatic fitting 11. The tissue-engaging member 30 has already been described in the first embodiment. Alternatively, other tissue-engaging members from other previous embodiments may also be substituted in place of tissue-engaging member 30.

As previously described, when the beating heart is "verticalized" by way of pericardium tissue retraction, the apex of the heart assumes a substantially protruding orientation outward from the patient's retracted chest cavity. The bracing means, preferably deployed in series after the deployment of the pericardium retraction device, serves as a stability-enhancing measure, which substantially limits the excursion or movement of a portion of the "verticalized" beating heart, preferably the apex. This bracing means may not be desired in all cardiac surgical interventions that are performed with the assistance of the pericardium retraction device.

Figure 10:
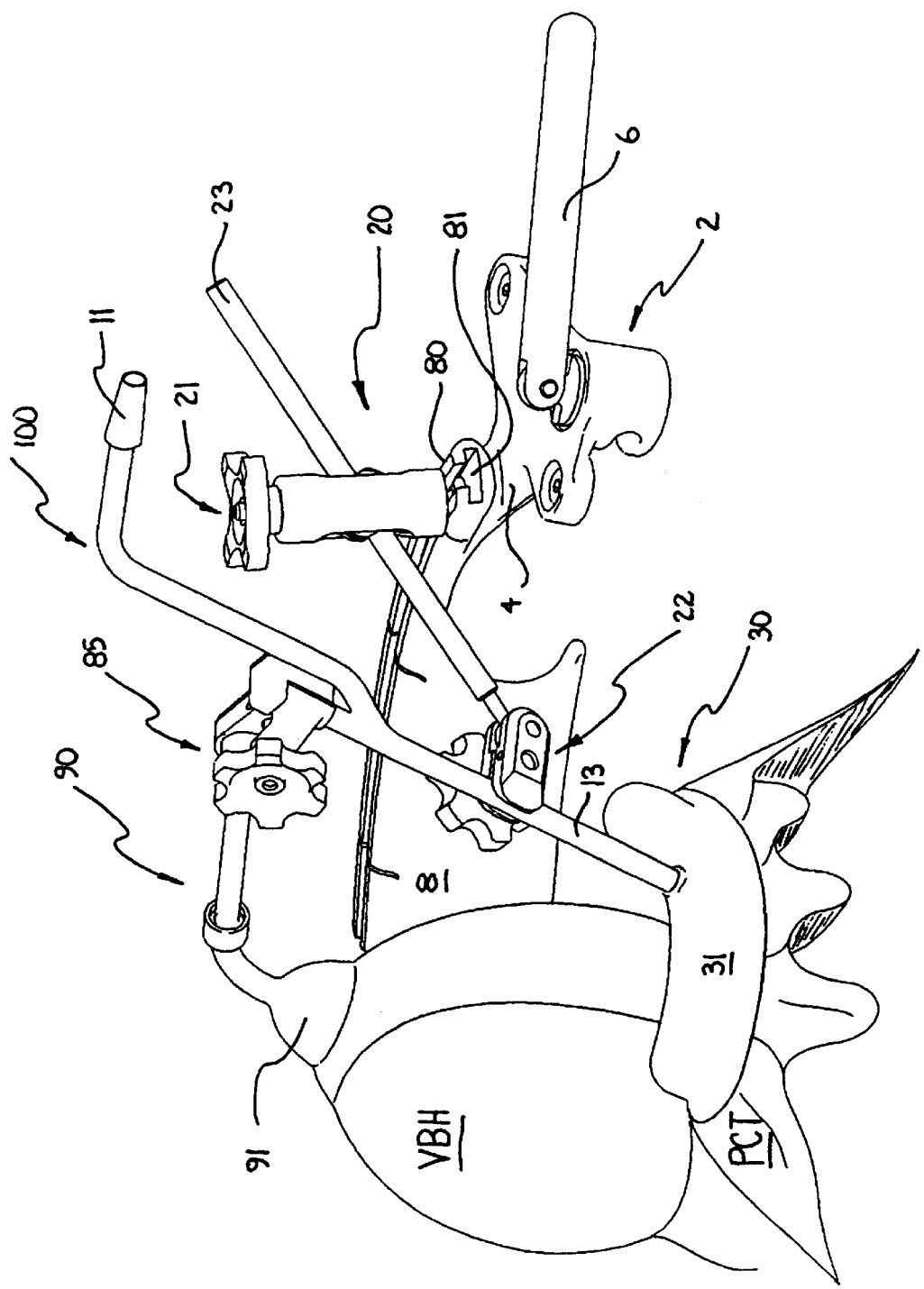
FIG. 10 is a perspective, elevational view of a pericardium retraction device according to a fourth embodiment of the present invention comprising a bracing member engaged with the apex of a beating heart.
Figure 11:
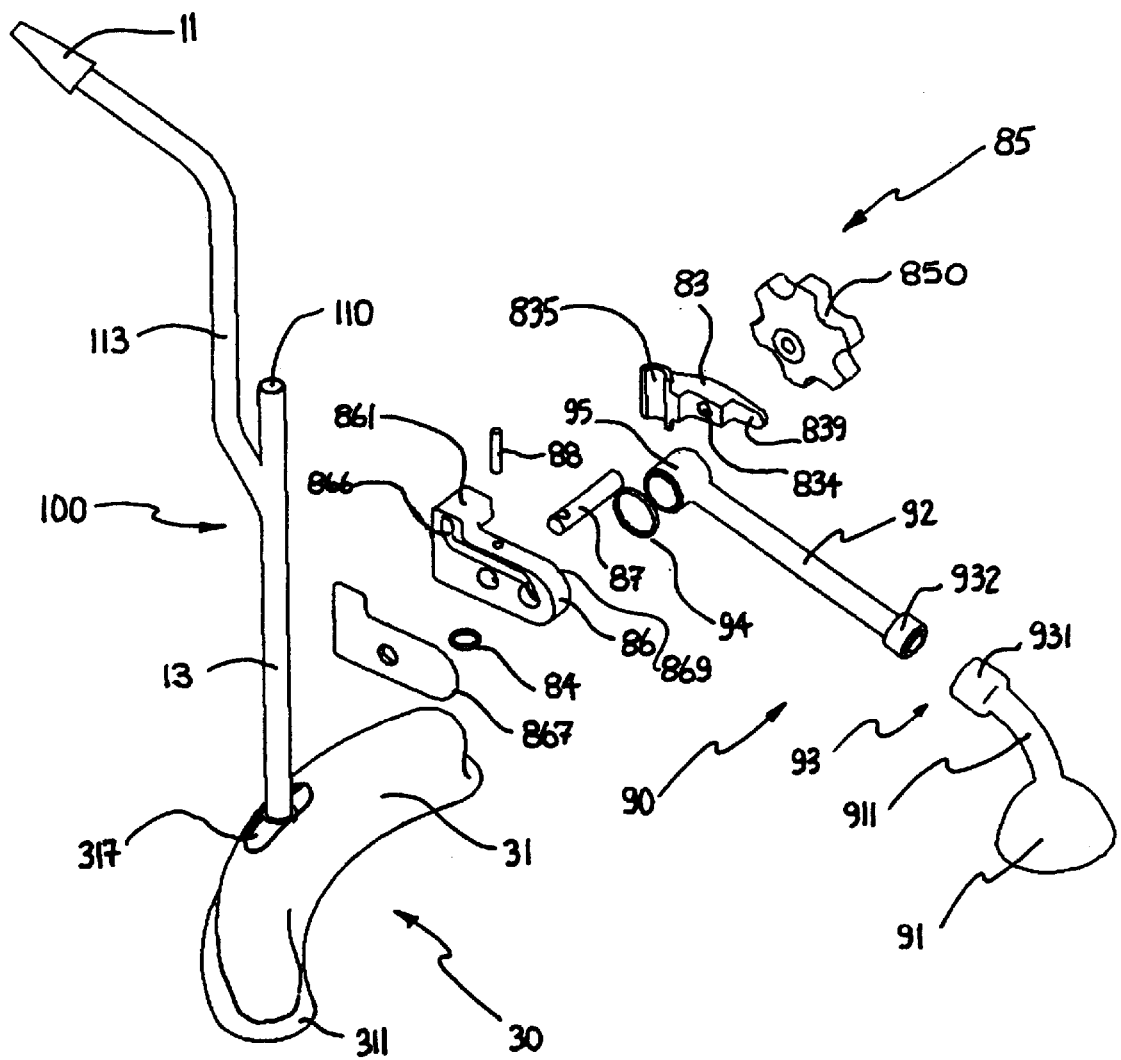
FIG. 11 is an exploded view of the pericardium retraction device and associated bracing member according to the fourth embodiment of the present invention illustrated in FIG. 10.

As illustrated in FIGS. 10 and 11, the apex-bracing mechanism 90 is comprised of an articulation and clamping member 85, a bracing or supporting shaft member 92, and a tissue-contacting member such as an apex-contacting member 91. The apex-bracing mechanism 90 is engaged with the pericardium retraction device 100 through the articulation and clamping member 85 which simultaneously clamps onto the proximal portion of shaft member 13 while securing the desired position and orientation of bracing shaft member 92. A negative pressure suction source is introduced through a pneumatic fitting 11 situated on the proximal end of extension shaft member 113. A conduit passage within extension shaft member 113 (not shown) supplies negative pressure to both the pericardium tissue-engaging member 30 through conduit passage 110 in shaft member 13, and the apex-contacting member 91 through substantially tubular bracing shaft member 92 and a series of passages hereunder described. Consequently, since it may be desired to deploy the apex-contacting member 91 subsequent to the pericardium tissue-engaging member 30, a valve means (like valve means 380 in the previous embodiment) is preferably contained within the said member 91.

With reference to FIG. 11, from the proximal end of conduit passage 110, the negative pressure supply enters a series of passages in the clamping member 86, more specifically into a plenum cavity 861 into which the proximal end of conduit passage 110 is received, through an integral transverse conduit passage 866, and through a conduit bore 869 which is disposed generally transverse to the axial direction of conduit passage 110. From the clamping member 86, the negative pressure supply enters into hollow articulation cylinder 95 and through internal passages in bracing shaft member 92 and resilient curved member 911 to attain the apex-contacting member 91 which, in this case, serves as a negative pressure suction port. Alternately, the apex contacting means 91 can be provided with its own designated negative pressure conduit line.

To maintain the negative pressure through component interfaces, a joint seal 84 is provided between clamping member 86 and the proximal end of shaft member 13 at the plenum cavity 861 location. A joint seal 94 is also provided between articulation cylinder 95 and clamping member 86 at the conduit bore 869 location. A counterbore (not shown) may be provided with conduit bore 869 in order to locate joint seal 94 and the contacting perimeter of articulation cylinder 95. Seal plate 867 is provided to cover conduit passage 866 and facilitate the machining of said conduit passages within clamping member 86. Alternatively, plate 867 may be eliminated if clamping member 86 is produced as a casting with integral cored conduit passages. Alternatively, extension shaft member 113 may be eliminated by extending shaft member 13 through the plenum cavity 861.

The articulation and clamping member 85 is comprised of clamping member 83 and clamping member 86. The securing of articulation and clamping member 85 is achieved through a threaded member 87, which is assembled in clamping member 86 through retaining pin 88 and extends through bore 834 of clamping member 83 to become engaged by tensioning knob 850. Shaft member 13 is engaged laterally by surface 835 and a like surface (not shown) of clamping members 83 and 86 respectively, and axially on its topmost surface by cavity plenum 861. This secures the orientation (rotation) of clamping member 85 and bracing shaft member 92 about the centerline of shaft member 13. Articulation cylinder 95 is simultaneously clamped between engagement surface 839 on clamp 83 and a like surface on clamp 86, thereby securing its articulation position in and out of chest cavity relative to shaft member 13 and clamping member 85.

Bracing shaft member 92 is comprised of an articulation cylinder 95 and an interface joint member 932. As illustrated in FIG. 11, bracing shaft member 92 is substantially tubular to integrate internal conduit passage for negative pressure when apex-contacting member 91 is a negative pressure suction port. Bracing shaft member 92 may be entirely rigid, or may be deformable only by a surgeon input, or may be a lockable multi-jointed articulated design and construction. In all variants, the said member 92 is substantially rigid in that it should not yield under the forces imposed on it by the beating heart.

Apex-contacting member 91 is comprised of a resilient curved member 911 and an interface joint member 931. Resilient curved member 911 is substantially flexible, since it will elastically yield a limited amount under the forces imposed by the beating heart, depending on its designed stiffness. FIGS. 12A to 12D illustrate variants in the apex-contacting member 91. FIG. 12A illustrates an apex-contacting member comprising a substantially conical cup made from a flexible polymeric material 915; FIG. 12B illustrates an apex-contacting member comprising a plurality of substantially rigid finger-like protrusions 916; FIG. 12C illustrates an apex-contacting member comprising a tissue-clamping means 917; and FIG. 12D illustrates an apex-contacting member comprising a substantially hemi-cylindrical cradle 918 with perforations to allow anchoring to the apex tissue of beating heart with an associated suture 919. Additionally, with each of these variants, a tissue-grasping means or hydrogel coating may also be incorporated on the heart contacting surface of the said apex-contacting member, in order to attempt to improve the adherence to the beating heart tissue. Any of the variants of FIGS. 12A, 12B and 12D may be utilized with the provision of a suction force or without.

The bracing shaft member 92 and apex-contacting member 91 are engaged at junction 93, which provides the ability to rotate apex-contacting member 91 about the centerline of shaft member 92. The two interface members 931 and 932 comprising the said junction 93 may be rotatingly engaged through suction, if the apex-contacting member 91 serves as a negative pressure suction port. Alternatively, interface members 931 and 932 may be rotatingly engaged through a magnetic attraction, through a press-fit allowing relative rotation of said interface members only through torque applied by surgeon's hand but not by loads exerted by the beating heart on said interface members, through a ratchet mechanism between said interface members, or by other like means.

In another variant of the present embodiment, junction 93 may be of a telescopic design to allow the translation, or the translation and rotation of apex-contacting member 91 relative to bracing shaft member 92.

Alternatively, a rotational interface replacing junction 93 may be incorporated in design of the articulation and clamping member 85. Alternatively, the articulation and clamping member 85 may be designed to allow the translation of bracing shaft member 92 along its longitudinal axis through said clamping member 85.

With reference to FIG. 10, to deploy the apex-bracing mechanism 90 the surgeon will preferably first position and orient the pericardium retraction device 100 in a similar manner as described in the previous embodiments. Once the beating heart is "verticalized", and the positioning and articulation mechanism 20 has been secured at both articulation members 21 and 22, the apex-bracing mechanism 90 is positioned and oriented within the same surgical workspace W, such that the apex-contacting member 91 is in contact with the apex of the beating heart and the articulation and clamping member 85 is engaged with the topmost surface and sides of shaft member 13. This may involve the rotation of the apex-bracing mechanism 90 about the centerline of shaft member 13, the articulation of bracing shaft member 92 about the centerline of articulation cylinder 95, and the rotation of apex-contacting member 91 about the centerline of bracing shaft member 92. The device is intended to allow for delicate presentation of the apex-bracing mechanism 90 preferably onto the apex of a "verticalized" beating heart.

The entire surgical apparatus assembly consisting of the pericardium retraction device 100 and the apex-bracing mechanism 90, may also be positioned and oriented within the surgical workspace W by way of adjustment of either of the second articulation member 22 or the first articulation member 21, or by way of simultaneous adjustment of both said articulation members 21 and 22. Consequently, the beating heart may be re-oriented and re-positioned through a displacement of both the pericardium retraction device 100 and apex-bracing mechanism 90.

Alternatively, clamping member 85 and articulation member 22 may be combined into one mechanical assembly, preferably when the apex-contacting member 91 does not serve as a negative pressure suction port. Clamping member 85 may be replaced with an interface sleeve that is clamped between the second articulation member 22 and shaft member 13.

Alternatively, in another embodiment, the apex-bracing mechanism 90 may be provided with its own designated positioning and articulation mechanism 20, comprising first 21 and second 22 articulation members, and whereby said first articulation member 21 may be slidingly and rotatingly engaged along rails 70, 80, or 50 of the sternum retractor 2, independently from the deployment of the pericardium retraction device 100.

Alternatively, the apex-bracing mechanism 90 may also be used exclusively in certain cardiac surgeries, without the pericardium retraction device 100.

Figure 13:
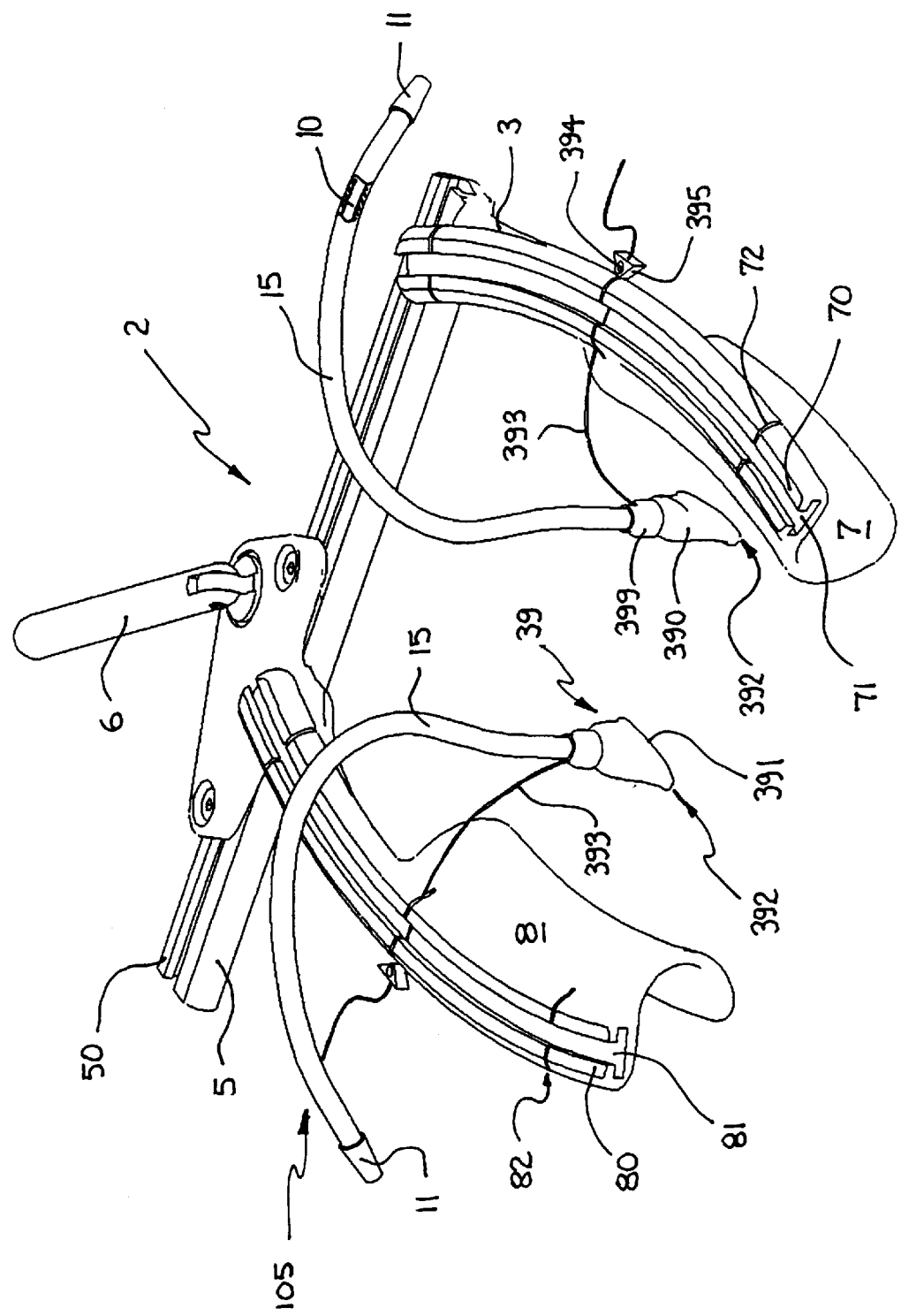
FIG. 13 is a perspective view of a pericardium retraction device according to a fifth embodiment of the present invention, comprising a plurality of independent tissue-engaging members.

FIG. 13 illustrates a fifth embodiment according to the present invention, showing a deployed surgical retractor 2 and deployed pericardium retraction device 105. The beating heart and pericardium tissue are not illustrated. The pericardium retraction device 105 is comprised of a tissue-engaging member 39, a device manipulating means in the nature of a wire-like filament 393, a conduit means such as flexible conduit 15, and a suction line interface means such as pneumatic fitting 11. The tissue-engaging member 39 is comprised of a deformable bell-shaped suction port 390 (illustrated in its deformed, deployed shape) and an attachment fitting 399. Suction port 390 is provided with the following main features: a tissue-engaging perimeter 391, at least one deformation bias 392 disposed preferably along said perimeter 391, and preferably a tissue-grasping means (not shown) on at least a portion of inside surface (not shown) of port 390 which comes into contact with the ingested pericardium tissue. With the exception of wire-like filament 393 described below, the suction port 390 is of similar construction to the suction port 36 of the second embodiment. The function of said port 390 and the cooperation of its constituent features having been previously described by similarity through the description of suction port 36 in the second embodiment.

In this embodiment, pericardium tissue is retracted by at least one pericardium retraction device 105. The beating heart is preferably "verticalized" by a plurality of tissue-engaging members 39, each supplied by its own designated conduit 15, and each being secured independently to a sternum retractor 2 through the anchoring of wire-like filament 393. The conduit 15 is a flexible tubular member tending to facilitate its placement within the surgical workspace W with an aim not to encumber access into the retracted chest cavity. Alternatively, conduit 15 may also be a malleable tubular member which the surgeon may deform into a desired less obstructive shape.

The proximal end of conduit 15 is configured with a pneumatic fitting 11 which may be connected to a negative pressure supply line in the operating room or to a negative pressure manifold along with several other pneumatic fittings when a plurality of pericardium retraction devices 105 are deployed. The suction port 39 is attached to conduit 15 through an attachment fitting 399, in either a demountable or permanent assembly as also described by similarity in the second embodiment. Negative pressure is supplied to the suction port 39 through an orifice feature in attachment fitting 399 which communicates with conduit passage 10 within conduit 15.

A wire-like filament 393 is attached to the attachment fitting 399 and serves as a device manipulating means allowing the surgeon to apply the desired tensile retraction load to the pericardium tissue by a pulling action on said wire-like filament. The desired pericardium retraction load to position and orient the beating heart is maintained during the surgical intervention by securing the free proximal end of filament 393 to sternum retractor 2, through a variety of anchoring mechanisms and methods. For instance, the free end of filament 393 may be inserted and partially threaded through an opening in a filament clamp 395. Filament clamp 395 is comprised of two cooperating jaws which exert a clamping load on the portion of filament 393 clamped therebetween. An adjustment means 394 is also provided within filament clamp 395, which when activated, serves to temporarily relieve the clamping action of two said jaws thereby allowing the repositioning of filament clamp 395 along the length of filament 393. The adjustment means 394 may be activated by a variety of methods, such as for instance through the application of a manual compression force on the adjustment means. Filament 393 is inserted in a slit-like channel 72 or 82. With the desired pulling action applied to the filament 393 to achieve pericardium retraction, the filament clamp 395 is repositioned along the length of filament 393 and brought into contact with spreader arm 3 or 4 of sternum retractor 2. By virtue of the imposed retraction load on pericardium tissue, clamp 395 is wedged against spreader arm 3 or 4 when filament wire 393 is inserted in slit-like channel 72 or 82. The clamping action of the jaws on filament 393 secures the resulting filament length between attachment fitting 399 and filament clamp 395 thereby maintaining the pericardium and resulting filament length in tension during the surgical procedure.

A variety of other methods may be used to secure the desired length of filament 393 relative to a portion of sternum retractor 2 in order to maintain the desired pericardium retraction load. For instance, the anchoring mechanisms described in copending Canadian patent application Serial No. 2,242,295 filed on Aug. 10, 1998 in the names of Paolitto et al. and entitled "Surgical Instruments for Tissue Retraction", for which a corresponding PCT application has been filed on Aug. 10, 1999 in the names of Paolitto et al. and entitled "Surgical Suture and Associated Anchoring Mechanism", the contents of which are incorporated herein by reference, may be used as they relate to the securing of a tensile loaded wire-like filament to a surgical retractor. These existing applications have been assigned to CORO-NEO Inc., the assignee of the present application.

Alternatively, a variant to the present fifth embodiment may consist of having one conduit 15 supplying negative pressure suction to more than one suction port 39 disposed at its distal end through a manifold type attachment fitting, as previously described.

Figure 14:
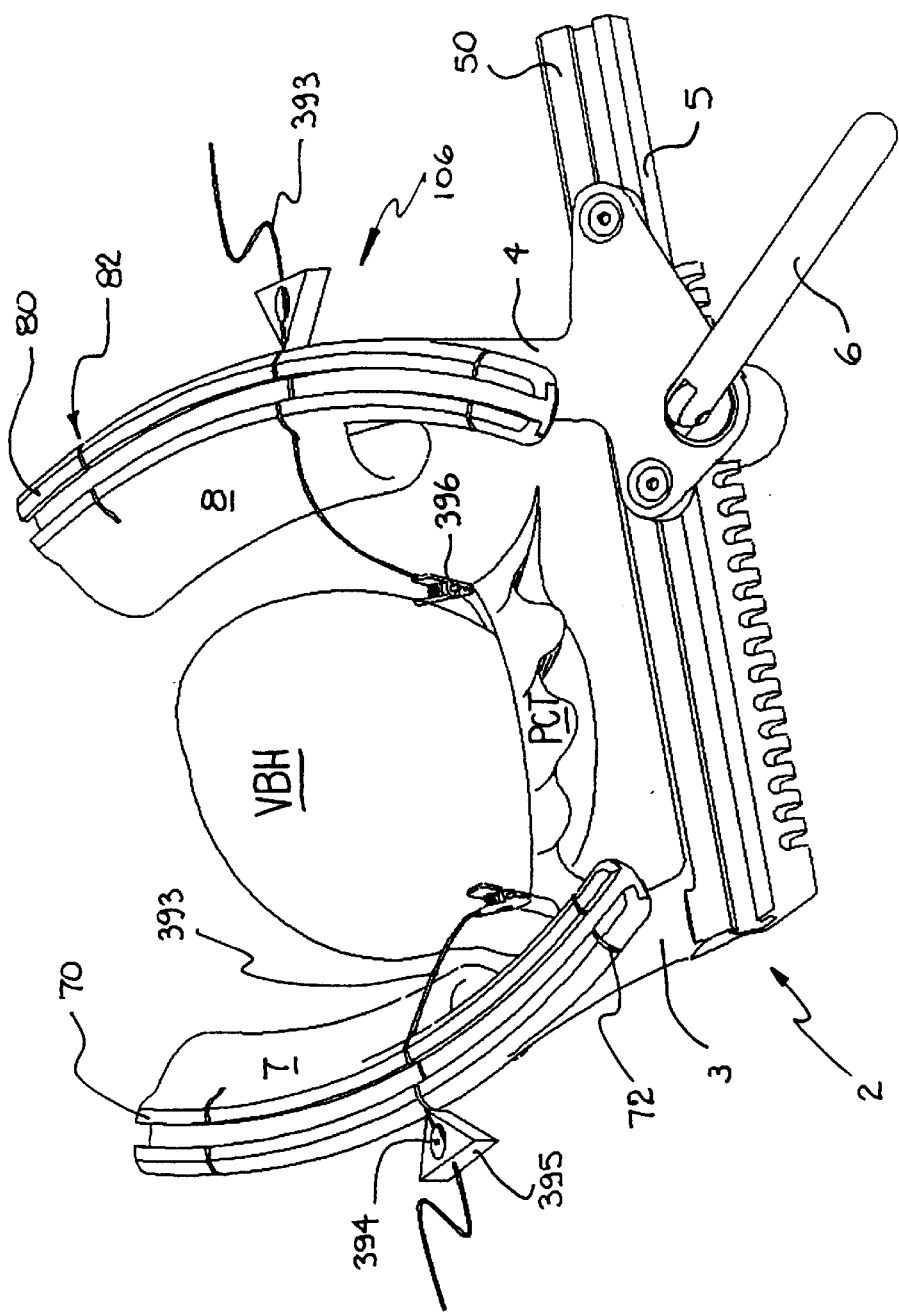
FIG. 14 is a perspective view of a pericardium retraction device according to a sixth embodiment of the present invention, comprising a plurality of independent tissue-clamping members.

FIG. 14 illustrates a sixth embodiment according to the present invention. In this embodiment, the deformable suction port 39 is replaced by an alternate mechanical tissue-engaging member such as a tissue clamp 396. The pericardium retraction device 106 is comprised of a tissue clamp 396, a device manipulating means in the nature of a wire-like filament 393, and an anchoring mechanism in the nature of a filament clamp 395.

The tissue clamp 396 is comprised of at least two clamping members which the surgeon or assistant manipulates in a manner to clamp therebetween a portion of the pericardium tissue. Examples include a snap-tight clamp or spring-loaded clamp. The tissue clamp 396 is engaged with pericardium tissue without having to pierce through said pericardium tissue, therefore tending to reduce the likelihood of inducing injury to underlying body tissue behind unraveled pericardium tissue.

The imposed clamping loads on the portion of pericardium tissue engaged within tissue clamp 396 is sufficient to overcome the retraction forces experienced during "verticalization" of the beating heart. The filament clamp 395 and adjustment means 394 are the same as those described in the fifth embodiment and may also be replaced by a variety of other anchoring mechanisms referred to above.

FIG. 15 illustrates a seventh embodiment according to the present invention. This embodiment incorporates a negative pressure conduit means into the positioning and articulation mechanism, with an aim to improving the ergonomics of the surgical workspace W. The pericardium retraction device 102 is comprised of a tissue-engaging member 30 (which is the same as in the first embodiment), a device manipulating means such as shaft member 131, and a conduit means such a conduit passage 10. The positioning and articulation mechanism 120 is similar to the positioning and articulation mechanism 20 of the previous embodiments except for the modifications introduced to incorporate a conduit means thereof. A pneumatic fitting 11 is provided on the proximal end of first positioning rod 25. An internal conduit passage 250 within rod 25 spans the entire length of the said rod, from the fitting 11 inlet to the spherical rod end 251. A flexible tubular coupling 253 plugs into the spherical rod end 251 of rod 25 at junction interface 252. The flexible tubular coupling 253 extends through a portion of shaft member 131 to communicate with conduit passage 10 within said shaft member 131. The pericardium retraction device 102 is engaged within the clamping members 262 of the second articulation member 26 and secured between said clamping members 262 by tensioning knob 261. The flexible tubular coupling 253 allows for a substantially similar deployment and substantially similar motion degrees of freedom of mechanism 120 relative to the positioning and articulation mechanism 20 of the previous embodiments.

In the embodiments of the present invention requiring a negative pressure supply, the source for this said negative pressure may be either a suction line generally available in operating rooms, or alternatively an auxiliary vacuum pump to provide an independent negative pressure supply or a pressure boost to the suction available in the operating room.

In the embodiments of the present invention described herein, it is intended to produce the bulk of the surgical apparatus from reusable components, whose assembly may be at least partially dismantled, if necessary, for ease of sterilization. All components are manufactured in either surgical grade stainless steel, titanium, aluminum or any other reusable sterilizable material suitable for surgical use. Components produced from polymeric materials are either reusable through specific sterilization procedures tailored to these component materials, or must be replaced after every use or after a predetermined number of uses if the polymeric material properties are not suitable for sterilization or degrade after repeated sterilization cycles. However, any number of the said reusable components may also be produced from disposable surgical grade plastics, if the case for disposable components is warranted and if the engineering and functional intent is maintained when the said component is produced from plastic.

Some of the features and principles of the embodiments of the present invention may advantageously be applied, if desired, to other surgical apparatus used for engaging body tissue through a negative pressure suction port. The above description of the embodiments of the present invention should not be interpreted in any limiting manner since variations and refinements are possible without departing from the spirit of the invention.

What is claimed is:

1. A surgical apparatus for retraction of tissue, the surgical apparatus comprising a tissue-engaging member for providing on the tissue a negative pressure suction force which is sufficient to retract same, the tissue-engaging member having a deformable skirt for contact with the tissue, the deformable skirt defining a contacting perimeter for substantially air-sealed engagement with the tissue, and wherein a first negative pressure plenum is formed within the deformable skirt when the tissue-engaging member is operatively connected to a negative pressure source and when the contacting perimeter of the deformable skirt is placed against the tissue in substantially air-sealed engagement therewith; the tissue-engaging member further providing a mechanism to prevent airflow through the deformable skirt when same is not in contact with the tissue.

2. The surgical apparatus according to claim 1, wherein said mechanism to prevent airflow comprises an air-impermeable member to delimit a second negative pressure plenum which is in airflow communication with the negative pressure source and which is located between the negative pressure source and the first negative pressure plenum, the said mechanism providing a valve which has a closed position and an open position, wherein the closed position prevents airflow communication between the first negative pressure plenum and the second negative pressure plenum, and wherein the open position permits such airflow communication, the valve being biased to its closed position and being activated to its open position when the deformable skit is brought into contact with the tissue.

3. The surgical apparatus according to claim 2, wherein the valve comprises a shaft having a terminal end for contact with the tissue, the shaft being in sliding engagement with an aperture therefor provided in said air-impermeable member, the shaft having a portion thereof characterized by a reduced diameter which is so disposed as to provide a substantially air-impermeable seal between the shaft and the aperture when the valve is in its biased closed position and to provide airflow communication through said portion thereof between the first negative pressure plenum and the second negative pressure plenum when the valve is activated to its open position.

4. The surgical apparatus according to claim 3, wherein the terminal end of the shaft of the valve projects outwardly beyond the contacting perimeter of the deformable skirt when the valve is in its biased closed position.

5. A surgical apparatus for attachment to a body tissue, said surgical apparatus being fluidly connectable to a vacuum source capable of creating a vacuum using a fluid, said surgical apparatus comprising:
   a tissue-engaging component, said tissue-engaging component including a generally concave vacuum compartment having a contacting peripheral edge for at least partially contacting a contacting portion of said body tissue;
   a fluid coupling arrangement mounted on said tissue-engaging component for fluidly coupling said vacuum compartment to said vacuum source;
   a valve in fluid communication with said fluid coupling arrangement, said valve being selectively operable between a valve open configuration and a valve closed configuration for respectively allowing and restricting fluid communication between said vacuum source and said vacuum compartment;
   whereby when said contacting peripheral edge is in a substantially seal-tight engagement with said contacting portion of said body tissue and said valve is in said valve open configuration, said vacuum source is allowed to generate a vacuum in said vacuum compartment for creating a suction attachment between said contacting peripheral edge and said contacting portion of said body tissue.

6. A surgical apparatus as recited in claim 5 further comprising a valve opening arrangement for urging said valve towards said valve open configuration upon said contacting peripheral edge reaching a predetermined spaced relationship relative to said contacting portion of said body tissue.

7. A surgical apparatus as recited in claim 6 wherein said valve opening arrangement biases said valve towards said valve open configuration upon said contacting peripheral edge contacting said contacting portion of said body tissue.

8. A surgical apparatus as recited in claim 5 further comprising a valve closing arrangement for urging said valve towards said valve closed configuration upon the sealing efficiency of the contact between said contacting peripheral edge and said contacting portion of said body tissue reaching a predetermined threshold.

9. A surgical apparatus as recited in claim 8 wherein said valve closing arrangement is calibrated so as to urge said valve towards said valve closed configuration upon said contacting peripheral edge being separated from said contacting portion.

10. A surgical apparatus as recited in claim 5 further comprising a biasing component for biasing said valve towards said valve closed configuration.

11. A surgical apparatus as recited in claim 5 wherein said valve is configured, sized and positioned so as to be biased towards said valve open configuration upon said contacting peripheral edge being put into contact with said contacting portion of said body tissue.

12. A surgical apparatus as recited in claim 5 wherein at least a portion of said valve protrudes outwardly beyond a geometrical plane intercepting said contacting peripheral edge when said valve is in said valve closed configuration.

13. A surgical apparatus as recited in claim 5 wherein said surgical apparatus defines a first cavity section being located adjacent said contacting peripheral edge and a second cavity section located intermediate said first cavity section and said vacuum source.

14. A surgical apparatus as recited in claim 5 wherein said vacuum compartment is divided into a compartment first section and a compartment second section, said compartment first section being located adjacent said contacting peripheral edge while said compartment second section is located intermediate said vacuum source and said compartment first section; said valve allowing communication of said fluid between said compartment first and second sections when said valve is in said valve open configuration and restricting communication of said fluid between said compartment first and second sections when said valve is in said valve closed configuration.

15. A surgical apparatus as recited in claim 14 wherein said vacuum compartment includes a compartment peripheral wall, said vacuum compartment also including a separation wall extending thereacross for separating said vacuum compartment into said compartment first and second sections; said separation wall being provided with a section aperture extending therethrough for allowing communication of said fluid between said compartment first and second sections, said section aperture defining an aperture peripheral edge; said valve including an obstructing component for selectively obstructing said section aperture so as to selectively allow and restrict the communication of said fluid between said compartment first and second sections through said section aperture.

16. A surgical apparatus as recited in claim 15 wherein said obstructing component includes a generally elongated plunger defining a plunger first end and a generally opposed plunger second end; said plunger also defining a plunger peripheral surface; said plunger being slidably positioned within said section aperture for movement between a plunger first position and a plunger second position; said plunger peripheral wall maintaining a generally sealing contact with said aperture peripheral edge when moved between said plunger first and second positions; said plunger being provided with a plunger channel extending from a position located adjacent said plunger first end to a position intermediate said plunger first and second ends; said plunger channel being configured and sized so that when said valve is in said valve open configuration said plunger is in said plunger first position with said channel extending through said section aperture to allow said fluid communication between said chamber first and second sections through said plunger channel; said plunger channel being also configured and sized so that when said valve is in said valve closed configuration said plunger is in said plunger second position restricting said fluid communication between said chamber first and second sections through said plunger channel.

17. A surgical apparatus as recited in claim 16 wherein said fluid coupling arrangement includes a fluid aperture formed in said compartment peripheral wall, said fluid aperture being in fluid communication with said compartment first section.

18. A surgical apparatus as recited in claim 17 further comprising a fluid coupling flange extending outwardly from said compartment peripheral wall adjacent said fluid aperture for facilitating the coupling of said vacuum source to said fluid aperture.

19. A surgical apparatus as recited in claim 16 further comprising a peripheral wall aperture extending through said compartment peripheral wall, a protruding section of said plunger located adjacent said plunger second end protruding outwardly from said vacuum compartment through said peripheral wall aperture; whereby a biasing force may be exerted on said protruding section for facilitating the movement of said plunger between said plunger first and second positions.

20. A surgical apparatus as recited in claim 16 further comprising a plunger biasing component coupled to said plunger for biasing said plunger towards said plunger second position.

21. A surgical apparatus as recited in claim 16 wherein at least a portion of said plunger protrudes outwardly beyond a geometrical plane intercepting said contacting peripheral edge when said plunger is in said plunger second position.

22. A surgical apparatus as recited in claim 16 wherein said plunger first end is provided with a plunger abutment section, said plunger abutment section being configured and sized so as to reduce the risks of inducing trauma to said body tissue upon said plunger abutment section contacting said body tissue.

23. A surgical apparatus as recited in claim 5 wherein said valve is coupled to an electronic arrangement for facilitating the operation of said valve between said valve open and closed configuration.

24. A surgical apparatus as recited in claim 23 wherein said electronic arrangement is coupled to a distance sensor for sensing the distance between a selected portion of said tissue-engaging component and said body tissue.

25. A surgical apparatus as recited in claim 24 wherein said distance sensor includes heat-measuring components.

26. A surgical apparatus as recited in claim 24 wherein said distance sensor includes light source components.

27. A surgical apparatus for attachment to a body tissue, said surgical apparatus being fluidly connectable to a vacuum source capable of creating a vacuum using a fluid, said surgical apparatus comprising:

at least two tissue-engaging components, each of said tissue-engaging components including a generally concave vacuum compartment having a contacting peripheral edge for at least partially contacting a corresponding contacting portion of said body tissue;

a fluid coupling arrangement attached to each of said tissue-engaging component for fluidly coupling said vacuum compartment to said vacuum source;

a vacuum distributing arrangement extending between said vacuum source and said tissue-engaging components for distributing the vacuum generated by said vacuum source to said at least two tissue-engaging component, said vacuum distributing arrangement allowing the intensity of the vacuum distributed to a given tissue-engaging component to be modulated depending on the efficiency of the seal between said contacting peripheral edge of said given tissue-engaging component and said corresponding contacting portion of said body tissue.

28. A surgical apparatus as recited in claim 27 wherein said vacuum distributing arrangement allows a given tissue-engaging component to be shut-off from said vacuum source upon the sealing efficiency of the contact between said contacting peripheral edge of said given tissue-engaging component and said corresponding contacting portion of said body tissue reaching a predetermined threshold.

29. A surgical apparatus as recited in claim 28 wherein said vacuum distributing arrangement is calibrated so as to prevent said vacuum from reaching said given tissue-engaging component upon said contacting peripheral edge of said given tissue-engaging component being separated from said corresponding contacting portion.

30. A surgical apparatus as recited in claim 27 wherein said vacuum distributing arrangement allows said vacuum to reach a given tissue-engaging component upon the contacting peripheral edge of said given tissue-engaging component reaching a predetermined spaced relationship relative to said corresponding contacting portion of said body tissue.

* * * * *